United States Patent
Lee et al.

(10) Patent No.: US 9,641,665 B2
(45) Date of Patent: May 2, 2017

(54) METHOD FOR PROVIDING CONTENT AND ELECTRONIC DEVICE THEREOF

(71) Applicant: Samsung Electronics Co., Ltd., Gyeonggi-do (KR)

(72) Inventors: Kwang-Hyeon Lee, Seoul (KR); Hyung-Rock Jung, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/838,600

(22) Filed: Aug. 28, 2015

(65) Prior Publication Data

US 2016/0065724 A1     Mar. 3, 2016

(30) Foreign Application Priority Data

Aug. 29, 2014    (KR) .................. 10-2014-0114325

(51) Int. Cl.
| | | |
|---|---|---|
| *H04M 1/00* | (2006.01) | |
| *H04M 1/725* | (2006.01) | |
| *A61B 5/024* | (2006.01) | |
| *A61B 5/16* | (2006.01) | |
| *A61B 5/00* | (2006.01) | |
| *G06F 19/00* | (2011.01) | |

(52) U.S. Cl.
CPC ..... *H04M 1/72569* (2013.01); *A61B 5/02438* (2013.01); *A61B 5/165* (2013.01); *A61B 5/6898* (2013.01); *G06F 19/3406* (2013.01); *A61B 5/0022* (2013.01); *A61B 5/681* (2013.01); *A61B 5/743* (2013.01); *A61B 5/7435* (2013.01); *H04M 1/7253* (2013.01); *H04M 1/72519* (2013.01)

(58) Field of Classification Search
CPC ... A61B 5/0022; A61B 5/02438; A61B 5/165; A61B 5/681; A61B 5/6898; A61B 5/743; A61B 5/7435; G06F 19/3406; H04M 1/72544; H04M 1/72569
USPC ............... 455/556.1, 41.1, 41.2, 423, 67.11; 600/509, 453, 374, 465, 485, 504, 587, 600/301, 300; 340/5.82; 348/333.01; 607/17, 4, 19; 482/8; 725/9; 702/19; 345/156
See application file for complete search history.

(56) References Cited

U.S. PATENT DOCUMENTS

| | | | | |
|---|---|---|---|---|
| 8,298,148 | B2 * | 10/2012 | Furman | A61B 5/0031 600/374 |
| 9,031,293 | B2 * | 5/2015 | Kalinli-Akbacak | G10L 25/63 382/128 |
| 2003/0139654 | A1 * | 7/2003 | Kim | A61B 5/02405 600/300 |

(Continued)

FOREIGN PATENT DOCUMENTS

| | | | |
|---|---|---|---|
| KR | 10-1027267 B1 | 4/2011 | |
| SE | EP 2108311 A1 * | 10/2009 | ......... A61B 5/02438 |

*Primary Examiner* — Tan H Trinh
(74) *Attorney, Agent, or Firm* — Cha & Reiter, LLC

(57) ABSTRACT

A method and an electronic device are provided herein. The electronic device includes a processor. The processor may execute the method, including detecting, by a sensor, heart rate information while providing a content of the electronic device, determining, by a processor, an emotional quotient based on the detected heart rate information, and mapping the determined emotional quotient to the provided content.

20 Claims, 21 Drawing Sheets

(56) References Cited

U.S. PATENT DOCUMENTS

| | | | |
|---|---|---|---|
| 2004/0111036 A1* | 6/2004 | Nissila | A61B 5/0006 600/509 |
| 2007/0203421 A1* | 8/2007 | Cho | A61B 5/0002 600/519 |
| 2008/0091515 A1* | 4/2008 | Thieberger | G06Q 10/063 705/7.11 |
| 2008/0096726 A1* | 4/2008 | Riley | A63B 24/0006 482/8 |
| 2008/0269958 A1* | 10/2008 | Filev | B60W 50/10 701/1 |
| 2009/0167677 A1* | 7/2009 | Kruse | A63B 24/0062 345/156 |
| 2010/0011388 A1* | 1/2010 | Bull | H04N 21/41407 725/9 |
| 2010/0085462 A1* | 4/2010 | Sako | G02B 27/017 348/333.01 |
| 2010/0086204 A1* | 4/2010 | Lessing | G06F 17/30265 382/165 |
| 2010/0113950 A1* | 5/2010 | Lin | A61B 5/02438 600/509 |
| 2010/0145203 A1* | 6/2010 | Kim | A61B 5/024 600/509 |
| 2011/0047508 A1* | 2/2011 | Metzler | G06F 19/322 715/810 |
| 2011/0183305 A1* | 7/2011 | Orbach | A61B 5/16 434/236 |
| 2011/0231767 A1* | 9/2011 | Russell | G06F 17/3087 715/733 |
| 2011/0261079 A1* | 10/2011 | Ingrassia, Jr. | A63B 24/0062 345/665 |
| 2012/0004575 A1* | 1/2012 | Thorn | G06F 3/011 600/587 |
| 2012/0116186 A1* | 5/2012 | Shrivastav | A61B 5/0507 600/301 |
| 2012/0323087 A1* | 12/2012 | Leon Villeda | A61B 5/165 600/301 |
| 2013/0013208 A1* | 1/2013 | Ohnemus | G06F 19/3431 702/3 |
| 2014/0112556 A1* | 4/2014 | Kalinli-Akbacak | G10L 25/63 382/128 |
| 2014/0143064 A1* | 5/2014 | Tran | A61B 5/0022 705/14.66 |
| 2014/0163396 A1* | 6/2014 | Jain | A61B 5/7282 600/484 |
| 2014/0200416 A1* | 7/2014 | Kashef | G06F 19/3418 600/301 |
| 2014/0247155 A1* | 9/2014 | Proud | H02J 7/025 340/870.16 |
| 2014/0287387 A1* | 9/2014 | Vukasinovic | G09B 7/02 434/236 |
| 2014/0331242 A1* | 11/2014 | De La Garza | H04N 21/44218 725/12 |
| 2014/0366049 A1* | 12/2014 | Lehtiniemi | H04N 21/44218 725/12 |
| 2015/0005653 A1* | 1/2015 | Michaelis | A61B 5/02438 600/519 |
| 2015/0018660 A1* | 1/2015 | Thomson | A61B 5/0404 600/393 |
| 2015/0099987 A1* | 4/2015 | Bhatkar | A61B 5/165 600/479 |
| 2015/0182130 A1* | 7/2015 | Utter, II | A61B 5/0205 600/483 |
| 2015/0190062 A1* | 7/2015 | Han | A61B 5/7221 600/479 |
| 2015/0195378 A1* | 7/2015 | Kano | G06F 17/30867 709/203 |
| 2015/0201065 A1* | 7/2015 | Shim | H04M 1/72569 455/556.1 |
| 2015/0215450 A1* | 7/2015 | Seo | H04L 67/22 455/566 |
| 2015/0242608 A1* | 8/2015 | Kim | G06F 1/3231 726/19 |
| 2015/0261775 A1* | 9/2015 | Shin | H04L 67/1097 707/827 |
| 2015/0342533 A1* | 12/2015 | Kelner | A61B 5/721 600/509 |
| 2016/0034042 A1* | 2/2016 | Joo | G02B 27/0172 345/633 |
| 2016/0081625 A1* | 3/2016 | Kim | H04W 4/008 600/301 |
| 2016/0113591 A1* | 4/2016 | Pijl | G08B 21/0453 340/870.07 |
| 2016/0142767 A1* | 5/2016 | Shigeta | H04N 21/4223 725/12 |
| 2016/0253710 A1* | 9/2016 | Publicover | G06Q 30/02 |

* cited by examiner

METHOD FOR PROVIDING CONTENT AND ELECTRONIC DEVICE THEREOF

CLAIM OF PRIORITY

The present application is related to and claims the benefit under 35 U.S.C. §119(a) of a Korean Patent Application Serial No. 10-2014-0114325, which was filed in the Korean Intellectual Property Office on Aug. 29, 2014, the entire disclosure of which is hereby incorporated by reference.

BACKGROUND

The present disclosure relates to a method and an apparatus for providing a content.

TECHNICAL FIELD

Electronic devices have gradually grown in complexity and capacity to perform one or more functions. Moreover, modern electronic devices are represented mainly by mobile terminals, more colloquially referred to as "smart phones". An electronic device such as a mobile terminal typically includes a large screen touch-sensitive display module and a high pixel camera module other than a basic function which is communication with a counterpart so that a still image or video can be photographed and a web surfing may be performed by connecting to a network. Recently, the electronic device further include a high-performance processor and thus can perform many diverse functions.

SUMMARY

An electronic device may acquire user heart rate information (e.g., a heart rate of a user of the electronic device) through a heart rate measurement sensor. Sometimes, the electronic device does not provide additional information beyond displaying the acquired heart rate information on a screen.

Accordingly, one aspect of the present disclosure is to provide a method and an apparatus for mapping an emotional quotient according to heart rate information to content and providing the mapped emotional quotient together when the content is provided.

In another aspect of the present disclosure, a method of operating an electronic device is provided. The method includes: detecting, by a sensor, heart rate information while providing a content of the electronic device, determining, by a processor, an emotional quotient based on the detected heart rate information, and mapping the determined emotional quotient to the provided content.

In another aspect of the present disclosure, an electronic device is provided. The electronic device includes a display, and a processor configured to: detect, by a sensor operatively coupled with the electronic device, heart rate information while providing content of the electronic device, determine an emotional quotient based on the detected heart rate information, and map the determined emotional quotient to the provided content.

BRIEF DESCRIPTION OF THE DRAWINGS

The present disclosure will be more apparent from the following detailed description taken in conjunction with the accompanying drawings, in which.

DETAILED DESCRIPTION

Figure 1:
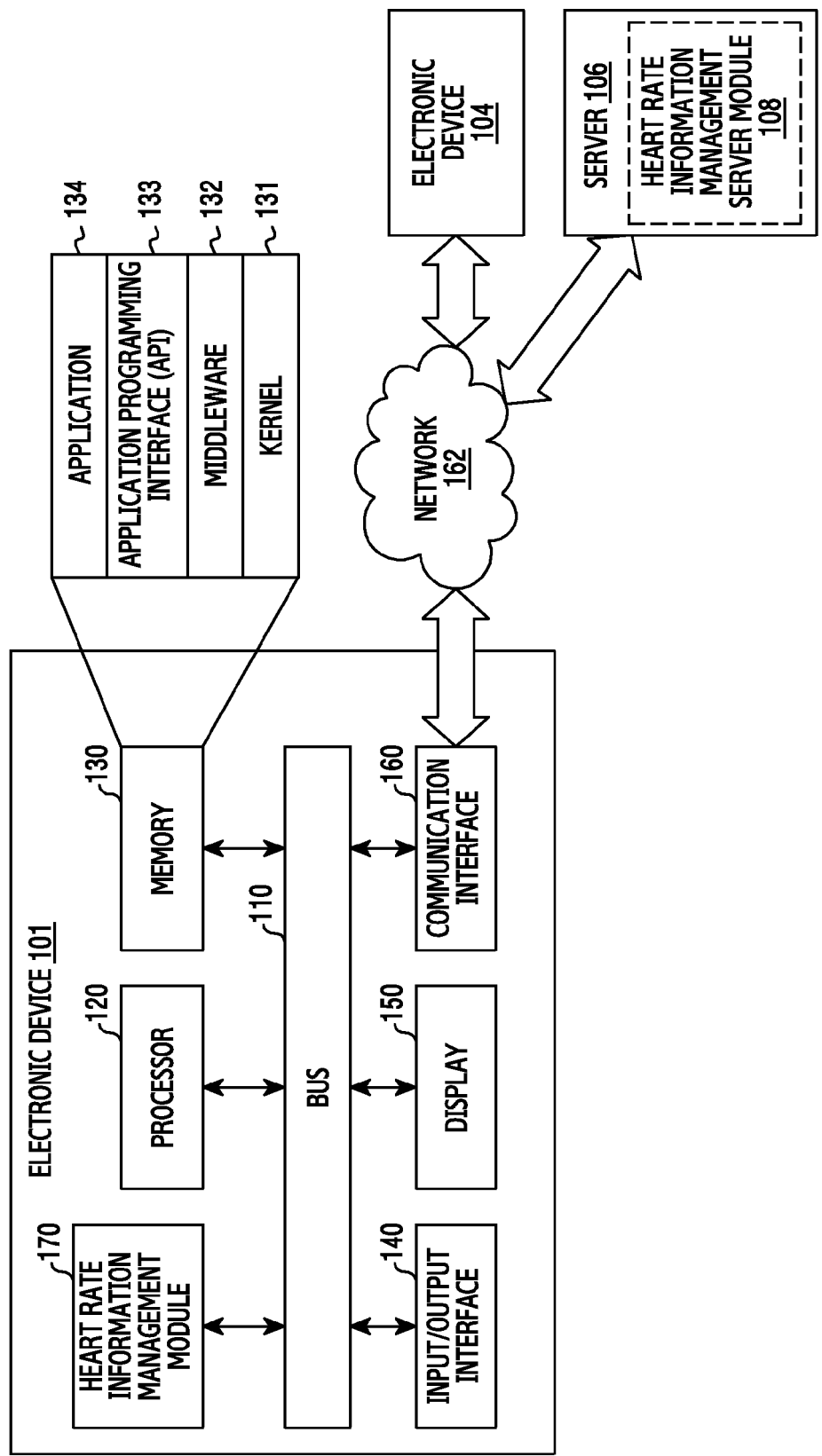
FIG. 1 is a view illustrating a network environment including an electronic device according to various embodiments of the present disclosure.

Hereinafter, various embodiments of the present disclosure will be described with reference to the accompanying drawings. The present disclosure may be modified in various forms and include various embodiments, but specific examples are illustrated in the drawings and described in the description. However, the description is not intended to limit the present disclosure to the specific embodiments, and it shall be appreciated that all the changes, equivalents and substitutions belonging to the present disclosure. In the description of the drawings, identical or similar reference numerals are used to designate identical or similar elements.

The term "include" or "may include" refers to the existence of a corresponding disclosed function, operation or component which can be used in various embodiments of the present disclosure and does not limit one or more additional functions, operations, or components. In the present disclosure, the terms such as "include" or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

In various embodiments of the present disclosure, the expression "or" or "at least one of A or/and B" includes any or all of combinations of words listed together. For example, the expression "A or B" or "at least A or/and B" may include A, may include B, or may include both A and B.

The expression "1", "2", "first", or "second" used in various embodiments of the present disclosure may modify various components of various embodiments but does not limit the corresponding components. For example, the above expressions do not limit the sequence and/or importance of the elements. The above expressions are used merely for the purpose of distinguishing an element from the other elements. For example, a first electronic device and a second electronic device indicate different electronic devices although both of them are electronic devices. For example, without departing from the present disclosure, a first component element may be named a second component element. Similarly, the second component element also may be named the first component element.

In the case where an element is referred to as being "connected" or "accessed" to other elements, it should be understood that not only the element is directly connected or accessed to the other elements, but also another element may exist between them. Meanwhile, in the case where an element is referred to as being "directly connected to" or "directly accessing" other elements, it should be understood that there is no element therebetween.

The terms in various embodiments of the present disclosure are used to describe a specific embodiment, and are not intended to limit the present disclosure. As used herein, the singular forms are intended to include the plural forms as well, unless the context clearly indicates otherwise.

Unless defined differently, all terms used herein, which include technical terminologies or scientific terminologies, have the same meaning as a person skilled in the art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present disclosure.

An electronic device according to various embodiments of the present disclosure may be a device with a communication function. For example, the electronic device may include at least one of a smart phone, a tablet Personal Computer (PC), a mobile phone, a video phone, an e-book reader, a desktop PC, a laptop PC, a netbook computer, a PDA, a Portable Multimedia Player (PMP), an MP3 player, a mobile medical device, a camera, a wearable device (for example, a Head-Mounted-Device (HMD) such as electronic glasses, electronic clothes, an electronic bracelet, an electronic necklace, an electronic appcessory, an electronic tattoo, and/or a smart watch.

According to some embodiments, the electronic device may be a smart home appliance with a communication function. The smart home appliance as an example of the electronic device may include at least one of a television, a Digital Video Disk (DVD) player, an audio, a refrigerator, an air conditioner, a vacuum cleaner, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, and/or an electronic picture frame.

According to some embodiments, the electronic device may include at least one of various types of medical devices (for example, Magnetic Resonance Angiography (MRA), Magnetic Resonance Imaging (MRI), Computed Tomography (CT), a scanning machine, ultrasonic wave device and the like), a navigation device, a Global Positioning System (GPS) receiver, an Event Data Recorder (EDR), a Flight Data Recorder (FDR), a car infotainment device, ship electronic equipment (for example, navigation equipment for a ship, a gyro compass and the like), avionics, a security device, and/or an industrial or home robot.

According to another embodiment, the electronic devices may include at least one of furniture or a part of a building/structure having a communication function, electronic boards, electronic signature receiving devices, projectors, or various measuring equipment (e.g., equipment for a water supply, an electricity, gases or radio waves).

An electronic device according to various embodiments of the present disclosure may be a combination of one or more of above described various devices. Also, an electronic device according to various embodiments of the present disclosure may be a flexible device. Also, an electronic device according to various embodiments of the present disclosure is not limited to the above described devices.

Hereinafter, an electronic device according to various embodiments will be described with reference to the accompanying drawings. The term "user" used in various embodiments may refer to a person who uses an electronic device or a device (for example, an artificial intelligence electronic device) that uses an electronic device.

FIG. 1 is a block diagram of an electronic device according to an embodiment of the present disclosure.

Referring to FIG. 1, the electronic device 101 may include a bus 110, a processor 120, a memory 130, an input/output interface 140, a display 150, a communication interface 160, and a heart rate information management module 170. According to an embodiment, the heart rate information management module 170 may be included in the processor 120 to operate or may be included in a separate module to interwork with the processor 120.

The bus 110 may be a circuit that interconnects the above-described components and delivers communications (for example, a control message) between the above-described components.

The processor 120 may, for example, receive a command from other components (for example, the memory 130, the input/output interface 140, the display 150, the communication interface 160, the heart rate information management module 170, etc.), through the bus 110, may decrypt the received command, and may execute operation or data processing based on the decrypted command.

The memory 130 may store a command or data received from the processor 120 or other components (for example, the input/output interface 140, the display 150, the communication interface 160, the heart rate information management module 170, and the like), or generated by the processor 120 or other components.

The memory 130 may include programming modules, for example, a kernel 131, a middleware 132, an Application Programming Interface (API) 133, an application 134, and the like. Each of the aforementioned programming modules may be formed of software, firmware, hardware, or a combination of at least two thereof.

According to an embodiment, the kernel 131 may control or manage system resources, for example, the bus 110, the processor 120, the memory 130, and the like, used for executing an operation or function implemented in other programming modules, for example, the middleware 132, the API 133, or the applications 134. Also, the kernel 131 may provide an interface that enables the middleware 132, the API 133, or the applications 134 to access an individual component of the electronic device 101 for control or management.

According to an embodiment, the middleware 132 may execute operate as a relay so that the API 133 or the applications 134 communicates to exchange data with the kernel 131. Also, in association with operation requests received from the application 134, the middleware 132 may execute a control, for example, scheduling or load balancing, for an operation request, through use of, for example, a method of assigning, to at least one of application 134, a priority of use of a system resource of the electronic device 101, for example, the bus 110, the processor 120, the memory 130, or the like).

According to an embodiment, the API 133 is an interface used by the applications 134 to control a function provided from the kernel 131 or the middleware 132, and may include, for example, at least one interface or function, for example, an instruction, for a file control, a window control, image processing, a character control, or the like.

According to an embodiment, the applications 134 may include a Short Message Service (SMS)/Multimedia Message Service (MMS) application, an e-mail application, a calendar application, an alarm application, a health care application (for example, an application for measuring a work rate or a blood sugar), an environment information application (for example, an application for providing atmospheric pressure, humidity, or temperature information). Additionally or alternatively, the application 134 may be an application associated with exchanging of information between the electronic device 101 and an external electronic device (for example, an electronic device 104). The application related to the information exchange may include, for example, a notification transmission application for transferring predetermined information to an external electronic device or a device management application for managing an external electronic device.

For example, the notification relay application may include a function of transferring, to the external electronic device, for example, the electronic device 104, notification information generated from other applications of the electronic device 101, for example, an SMS/MMS application, an e-mail application, a health management application, an environmental information application, and the like. Additionally or alternatively, the notification relay application may receive notification information from, for example, an external electronic device (for example, the electronic device 104), and may provide the notification information to a user. For example, the device management application may manage (for example, install, delete, or update) a function for at least some parts of the external electronic device (for example, the electronic device 104) communicating with the electronic device 101 (for example, a function of turning on/off the external electronic device itself, (or some components,) or a function of adjusting luminance (or a resolution) of the display), applications operating in the external electronic device, or services provided by the external electronic device (for example, a call service and a message service).

According to various embodiments, the applications 134 may include an application designated based on properties (for example, a type of electronic device) of an external electronic device (for example, the electronic device 104). For example, when the external electronic device is an MP3 player, the application 134 may include an application related to the reproduction of music. Similarly, when the external electronic device is a mobile medical device, the application 134 may include an application related to health care. According to an one embodiment, the applications 134 may include at least one of applications received from an application designated for the electronic device 101 or an application received from an external electronic device (for example, a server 106 or the electronic device 104).

According to an embodiment, the input/output interface 140 may transfer a command or data input by a user through an input/output device (for example, a sensor, a keyboard, or a touch screen) to the processor 120, the memory 130, the communication interface 160, and the heart rate information management module 170, for example, through the bus 110. For example, the input/output interface 140 may provide, to the processor 120, data associated with a touch of a user input through a touch screen. Further, the input/output interface 140 may output, for example, command or data received through the bus 110 from the processor 120, the memory 130, the communication interface 160, and the heart rate information management module 170, to an input/output device (for example, a speaker or display). For example, the input/output interface 140 may output voice data processed by the processor 120 to the user through a speaker.

According to an one embodiment, the display 150 may display various pieces of information (for example, multimedia data, text data, and the like) to a user.

According to one embodiment, the communication interface 160 may connect communication between the electronic device 101 and an electronic device (for example, the electronic device 104 or the server 106). For example, the communication interface 160 may be connected to the network 162 through wireless communication or wired communication, and may communicate with an external device. The wireless communication may include at least one of, for example, Wi-Fi, Bluetooth (BT), Near Field Communication (NFC), Global Positioning System (GPS) and/or cellular communication (for example LTE, LTE-A, CDMA, WCDMA, UMTS, WiBro, GSM, etc.). The wired communication may include at least one of, for example, a Universal Serial Bus (USB), a High Definition Multimedia Interface (HDMI), a Recommended Standard 232 (RS-232), and/or a Plain Old Telephone Service (POTS).

According to one embodiment, the network 162 may be a communication network. The telecommunication network may include at least one of a computer network, Internet, Internet of things, and/or a telephone network. According to an one embodiment, a protocol (for example, a transport lay protocol, data link layer protocol, or a physical layer protocol) for communication between the electronic device 101 and the external device may be supported by at least one of the applications 134, the application programming interface 133, the middleware 132, the kernel 131, and/or the communication interface 160.

According to an embodiment, a server 106 performs at least one operation (or function) implemented in an electronic device 101 to support an operation of the electronic device 101. For example, the server 106 may include a heart rate information management server module 108 which supports a heart rate information management module 170 implemented in the electronic device 101. For example, the heart rate information management server module 108 includes at least one component of the heart rate information management module 170 and then may perform (e.g., deputize) at least one operation of operations which the heart rate information management module 170 also performs.

The heart rate information management module 170 may perform an operation of acquiring heart rate information when content is provided, an operation of determining an emotional quotient on the basis of the acquired heart rate information, and an operation of mapping the determined emotional quotient to the content.

The heart rate information management module 170 may perform an operation of identifying whether the emotional quotient mapped to a content exists when the content is provided and an operation of providing the emotional quotient mapped to the content.

Additional information on the heart rate information management module 170 will be provided through FIG. 2 described below.

Figure 2:
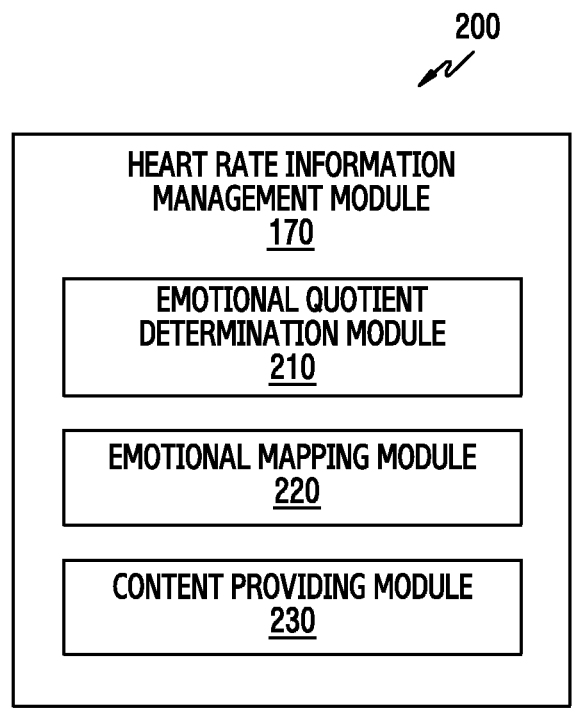
FIG. 2 is a block diagram illustrating a heart rate information management module of an electronic device according to various embodiments of the present disclosure.

FIG. 2 is a block diagram 200 illustrating a heart rate information management module 170 of an electronic device (for example, electronic device 101) according to various embodiments of the present disclosure.

Referring to FIG. 2, the heart rate information management module 170 may include an emotional quotient determination module 210, an emotional mapping module 220, and a content providing module 230.

The emotional quotient determination module 210 may determine an emotional quotient on the basis of user heart rate information acquired from an electronic device (e.g., electronic device 101) or an external electronic device (e.g., electronic device 104) connected to the electronic device, when the electronic device provides a content.

The emotional mapping module 220 may map an emotional quotient determined in the emotional quotient determination module 210 to the content.

The content providing module 230 may provide an emotional quotient mapped to the content by the emotional mapping module 220 together with a corresponding content.

Figure 3:
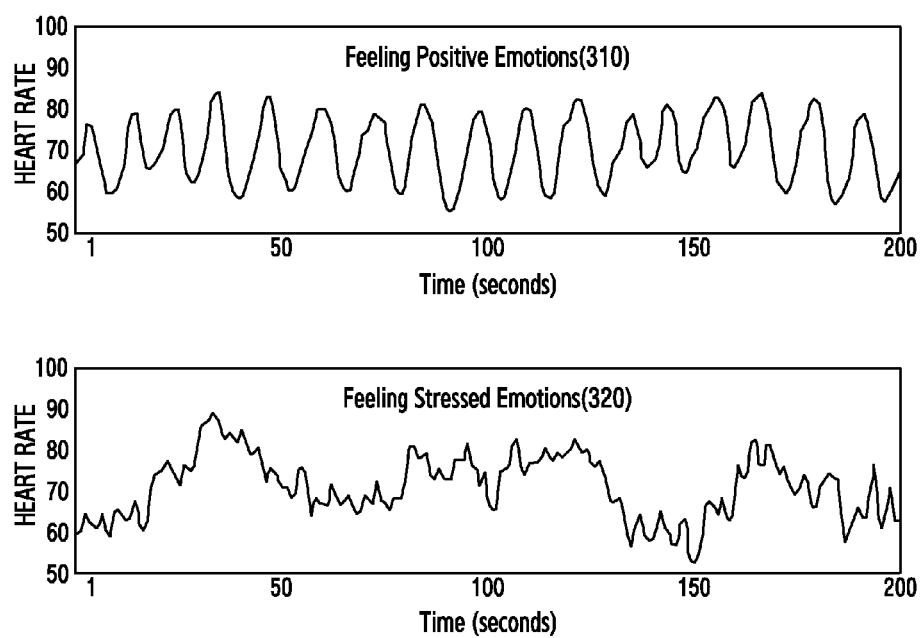
FIG. 3 is a graph illustrating a heart rate change according to an emotional state in an electronic device according to various embodiments of the present disclosure.

FIG. 3 is a graph illustrating a heart rate change according to an emotional state in an electronic device according to various embodiments of the present disclosure.

Referring to FIG. 3, an electronic device (e.g., electronic device 101) may determine whether an emotional state is in a peaceful state 310 or a stressed state 320 on the basis of user heart rate information. Herein, even though two examples of the emotional state determined on the basis of the user's heart rate information have been described, other diverse example emotional states determined on the basis of heart rate information are contemplated in various alternative embodiments of the present disclosure. According to an embodiment, the electronic device may determine user's various emotional states such as calmness, happiness, anger, fatigue, sadness, surprise, pain, thrill and others on the basis of heart rate information.

Figure 4:
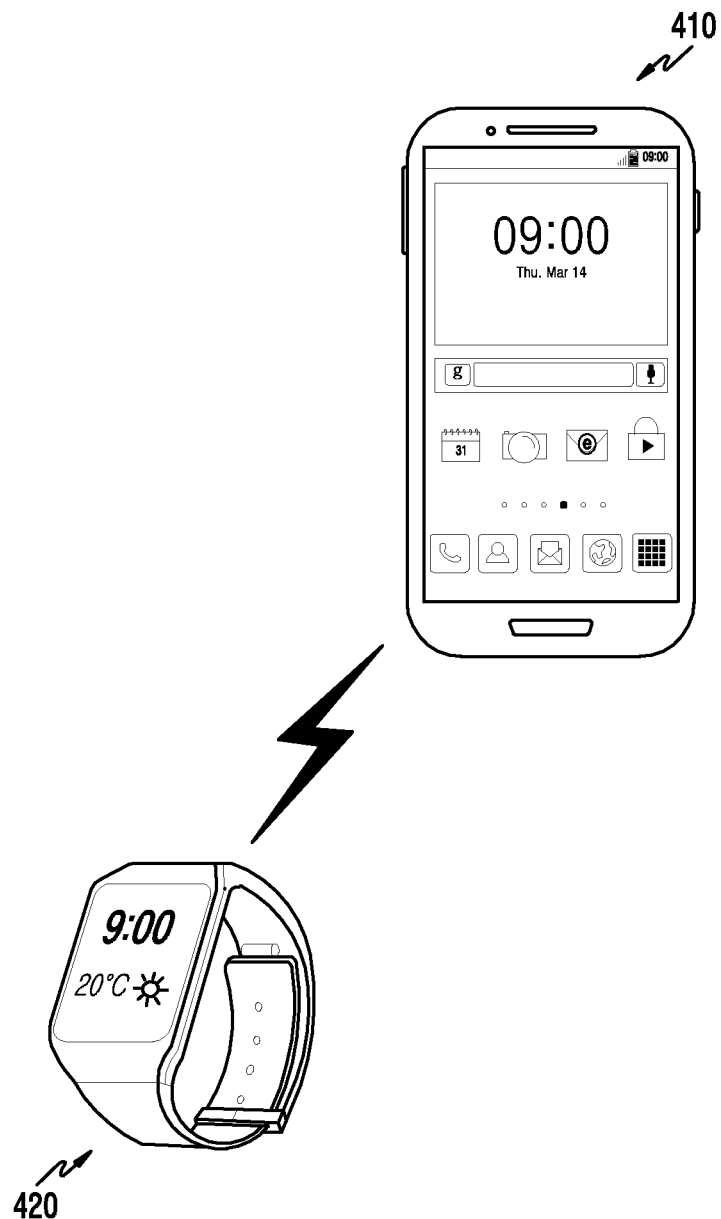
FIG. 4 is a view illustrating a method of acquiring user heart rate information in an electronic device according to various embodiments of the present disclosure.

FIG. 4 is a view illustrating a method of acquiring user heart rate information in an electronic device according to various embodiments of the present disclosure.

Referring to FIG. 4, an electronic device 410 may acquire user heart rate information through a heart rate measurement sensor included in the electronic device 410. According to an embodiment, the electronic device 410 may acquire the user's heart rate information through an external electronic device 420 communicatively connected or otherwise operatively coupled to the electronic device 410. According to an embodiment, the external electronic device 420 may transmit heart rate information measured from the external electronic device 420 to the electronic device 410 through wireless communication, in response to a transmission request of the electronic device 410. According to an embodiment, the electronic device 410 may transmit heart rate information measured from the electronic device 410 to the external electronic device 420 through wireless communication, on the basis of (or in response to) a transmission request of the external electronic device 420. Although two examples of a method of acquiring the user heart rate information have been described, it is understood that other diverse methods of obtaining heart rate information may be utilized in other various embodiments according to the present disclosure.

Figure 5:
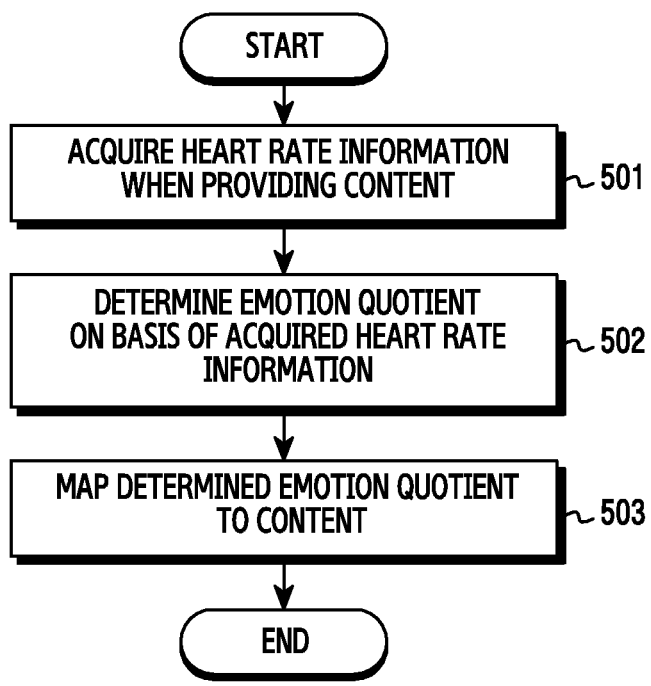
FIG. 5 is a flow chart illustrating a procedure for mapping an emotional quotient to a content in an electronic device according to various embodiments of the present disclosure.

FIG. 5 is a flow chart illustrating a procedure for mapping an emotional quotient to a content in an electronic device according to various embodiments of the present disclosure.

Referring to FIG. 5, in operation 501, an electronic device (e.g., electronic device 101) may acquire heart rate information when a content is provided. According to one embodiment, content may include at least one of services provided by the electronic device, such as a call function, an electronic book, or playback of a music and/or a video, or execution of an application. In various embodiments of the present disclosure, even though content provided by the electronic device has been described as an example, it is understood the disclosure is not limited thereto.

According to one embodiment, when providing the content, the electronic device may then acquire heart rate information for a user who utilizing the electronic device (or an external electronic device) to receive the content, where the electronic device (or external electronic device) includes a heart rate sensor. According to an embodiment, the electronic device may receive user heart rate information acquired from the electronic device (or external electronic device—e.g., electronic device 104) communicatively connected to the electronic device.

In operation 502, the electronic device may determine an emotional quotient based on the acquired heart rate information. According to one embodiment, the electronic device may determine (or detect) an emotion corresponding to and based on the heart rate information currently acquired for each piece of a preconfigured emotion. According to an embodiment, the electronic device may convert the determined emotion into an icon and/or a numerical value.

In operation 503, the electronic device may map the determined emotional quotient to some content. According to an embodiment, the electronic device maps an emotional quotient based on user acquired heart rate information to a corresponding content while providing a current content so that the emotional quotient mapped to the corresponding content can be provided to a user in providing the corresponding content later.

Hereinafter, various embodiments will be described in which, in an electronic device, an emotional quotient is mapped to content when the content is provided, and when a corresponding content is provided, it is provided together with the mapped emotional quotient.

Figure 6:
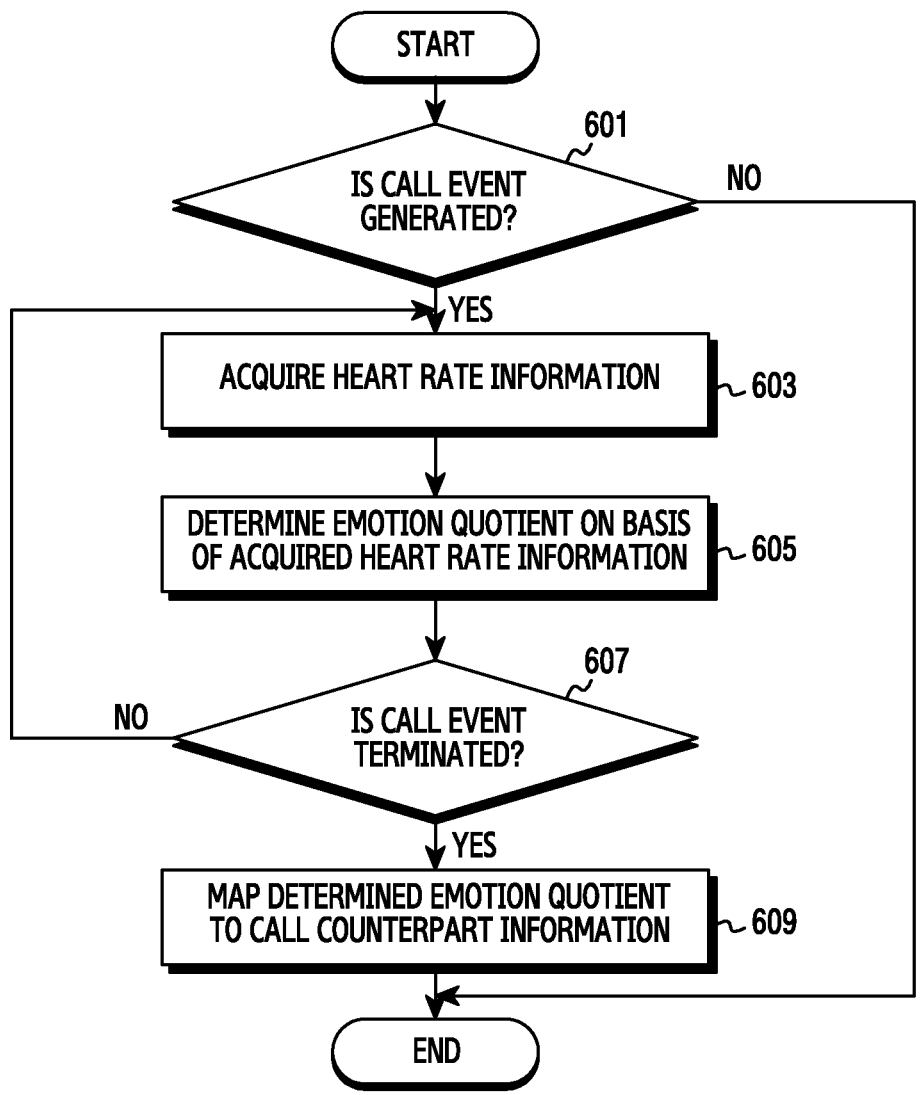
FIG. 6 is a flow chart illustrating a procedure for mapping an emotional quotient for each call in an electronic device according to various embodiments of the present disclosure.

FIG. 6 is a flow chart illustrating a procedure for mapping an emotional quotient for each call in an electronic device according to various embodiments of the present disclosure.

Referring to FIG. 6, in operation 601, an electronic device (e.g., electronic device 101) may identify whether a call event is generated. According to an embodiment, an electronic device may identify whether a voice or video call event is generated. According to an embodiment, the electronic device may identify whether an outgoing or incoming call event is generated.

In operation 603, the electronic device may acquire heart rate information. According to an embodiment, the electronic device may acquire user heart rate information through a heart rate sensor included in the electronic device. According to an embodiment, the electronic device may acquire user heart rate information through an external electronic device communicatively connected to the electronic device.

In operation 605, the electronic device may determine an emotional quotient for the user on the basis of the acquired heart rate information. According to an embodiment, the electronic device may determine an emotional quotient corresponding to heart rate information acquired during or within a reference time interval. For example, the electronic device may determine an emotion quotient based on heart rate information acquired during an interval defined by, for example, a current time point from N seconds to the current time point. In another example, the electronic device may determine an emotion quotient based on heart rate information acquired during or within an interval spanning from a call start time point to a current time point.

In operation 607, the electronic device may identify whether a call event is terminated. When the call event is not terminated, the electronic device may continue to monitor and acquire heart rate information, as described in operation 603. That is, the electronic device may periodically acquire user heart rate information until the call is terminated and determine an emotional quotient based on the acquired heart rate information.

In operation 609, the electronic device may map the determined emotional quotient to counterpart information. According to an embodiment, the electronic device may store an emotion quotient based on user heart rate information acquired during an execution of a call within counterpart information (e.g., contact number, or the like). According to an embodiment, the electronic device may store a corresponding emotional quotient with the counterpart information particularly when a call is performed over the reference time interval.

Figure 7:
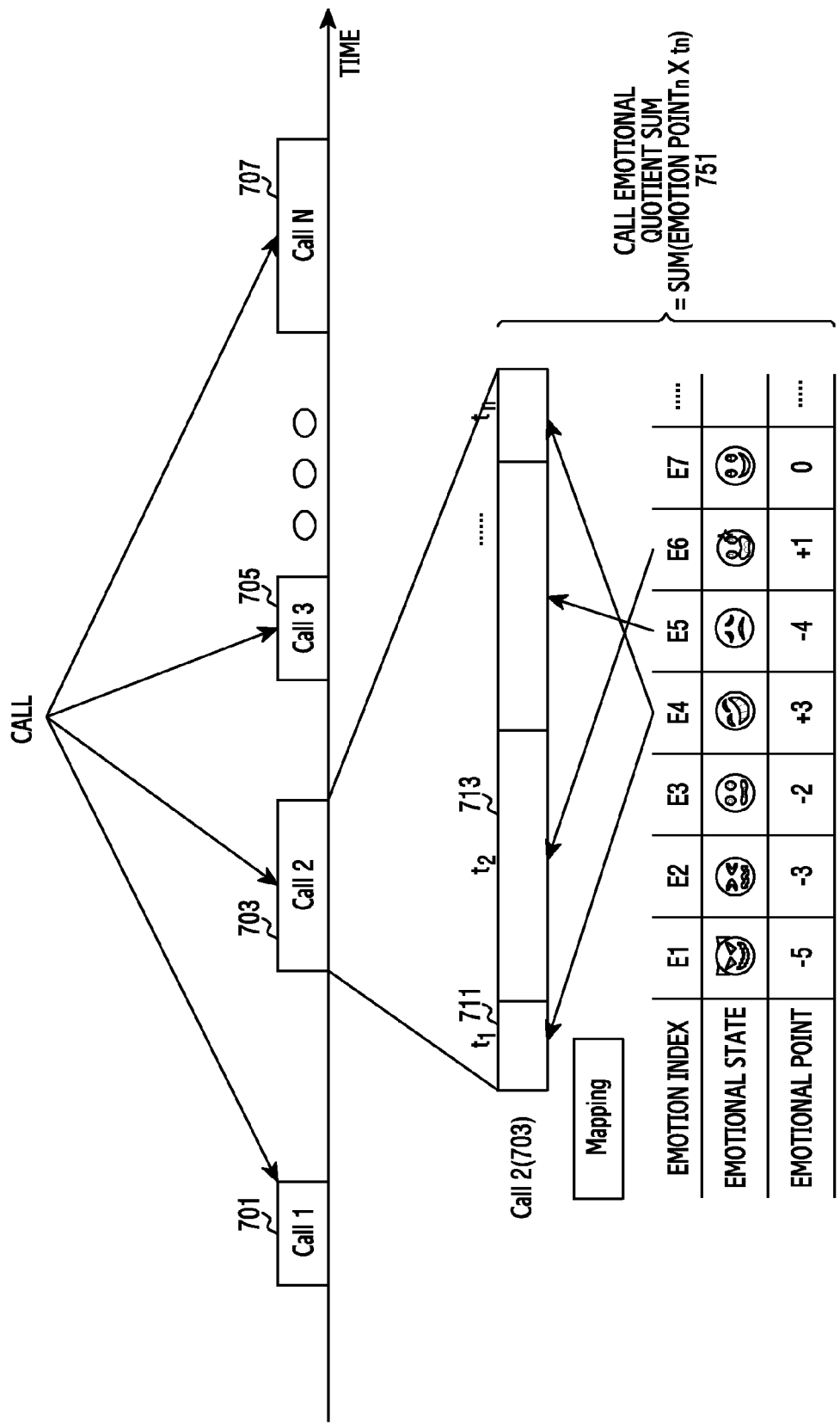
FIG. 7 is a view illustrating a method of determining an emotional quotient for each call in an electronic device according to various embodiments of the present disclosure.

FIG. 7 is a view illustrating a method of determining an emotional quotient for each call in an electronic device according to various embodiments of the present disclosure.

Referring to FIG. 7, for example, an operation will be described for determining an emotional quotient for a second call information 703, which is one of multiple pieces of call information 701, 703, 705, and 707 stored in an electronic device (e.g., electronic device 101).

According to one embodiment, the electronic device may determine that user emotion corresponds to "E4" during a time interval "t1" 711 and user emotion corresponds to E6 during a time interval "t2" 713, for the second call information 703 representing the duration of the second call.

According to an embodiment, the electronic device may determine a call emotional quotient 751 for the entirety of second call information 703. For example, one method of determining the call emotion quotient 751 is to calculate a numerical value by multiplying a duration (e.g., "t2" 713) on which one emotion (e.g., E6) is maintained in during a portion of a call information representing a length of a call (e.g., the second call information 703) by a point of a corresponding emotion (e.g., −4). That is, when multiple emotions exist in one call, the electronic device may calculate a numerical value by multiplying a duration on which each emotion is maintained by a point corresponding to each emotion, and adding each numerical value to determinate an emotional quotient. According to one embodiment, the electronic device may calculate an average of points for each emotion included in one call information and then determine an overall or average emotion for the corresponding call information.

Figure 8:
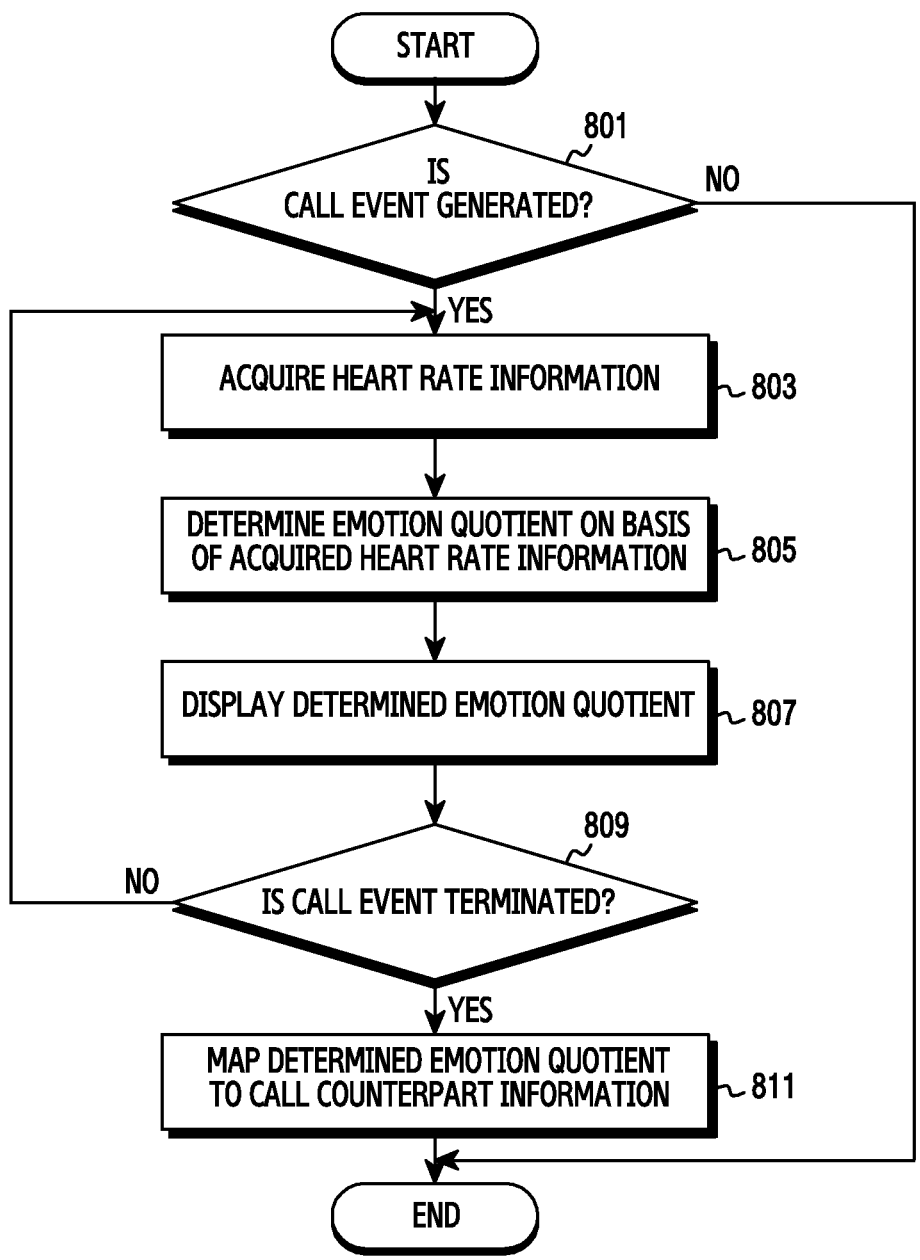
FIG. 8 is a flow chart illustrating a procedure for mapping and providing an emotional quotient for each call in an electronic device according to various embodiments of the present disclosure.

FIG. 8 is a flow chart illustrating a procedure for mapping and providing an emotional quotient for each call in an electronic device according to various embodiments of the present disclosure.

Referring to FIG. 8, in operation 801, an electronic device (e.g., electronic device 101) may identify whether a call event is generated. According to one embodiment, an electronic device may identify whether a voice or video call event is generated. According to another embodiment, the electronic device may identify whether an outgoing or incoming call event is generated.

In operation 803, the electronic device may acquire heart rate information. According to one embodiment, the electronic device may acquire user heart rate information through a heart rate sensor included in the electronic device. According to another embodiment, the electronic device may acquire user heart rate information through an external electronic device in communication with the electronic device.

In operation 805, the electronic device may determine an emotional quotient on the basis of the acquired heart rate information. According to an embodiment, the electronic device may determine an emotional quotient corresponding to heart rate information acquired during a reference time interval. For example, the electronic device may determine an emotion quotient on the basis of heart rate information acquired during an interval starting from a current time point to N seconds before the current time point. In another example, the electronic device may determine an emotion quotient on the basis of heart rate information acquired during an interval from a call start time point to a current time point.

Figure 9:
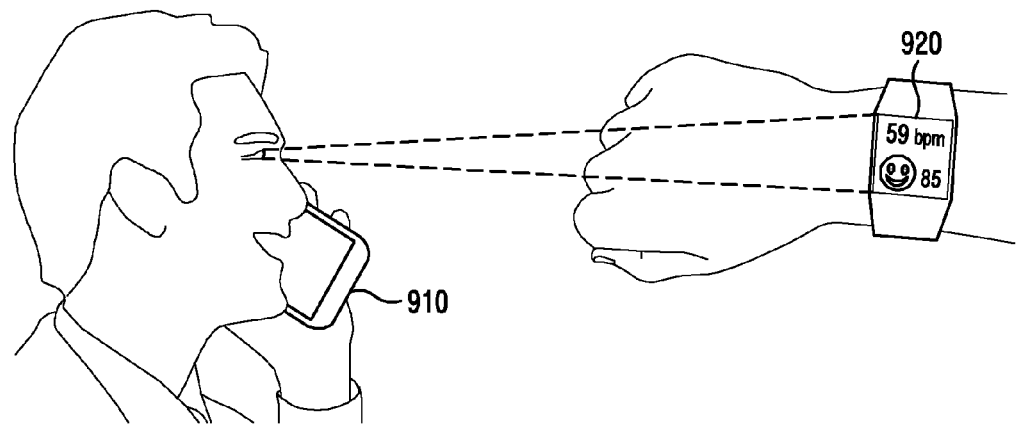
FIG. 9 is a view illustrating a method of providing an emotional quotient during a voice call in an electronic device according to various embodiments of the present disclosure.
Figure 10:
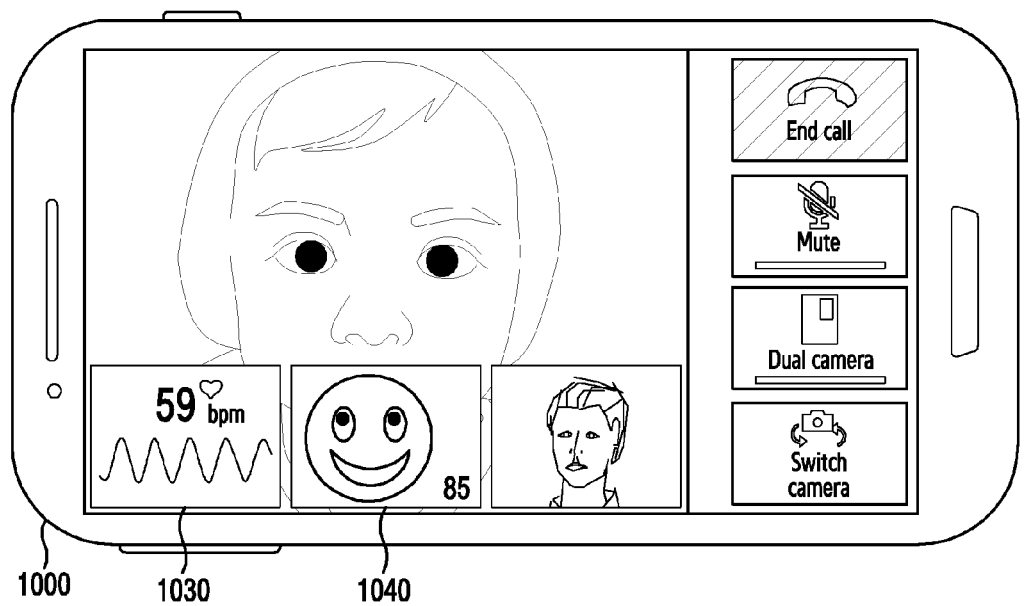
FIG. 10 is a view illustrating a method of providing an emotional quotient during a video call in an electronic device according to various embodiments of the present disclosure.

In operation 807, the electronic device may display the emotional quotient determined based on the acquired heart rate information. For example, according to one embodiment, as shown in FIG. 9, an external electronic device 912 may display an emotional quotient detected based on heart rate information acquired while performing a call of a counterpart through the heart rate sensor of an external electronic device 920 connected to the electronic device 910. That is, the external electronic device 920 may include a display installed thereto for display of the heart rate information and/or the emotional quotient, as seen in FIG. 9. According to one embodiment, as shown in FIG.

10, when an electronic device 1000 provides a video call service, the electronic device 1000 may display an emotional quotient 1040, which is determined on the basis of the heart rate information acquired during a video call with a counterpart, on a screen of the electronic device 1000. Additionally, the electronic device 1000 may display heart rate information 1030 in real time.

In operation 809, the electronic device may identify whether the call event is terminated. When the call event is not terminated, the electronic device may continue to acquire heart rate information as described in operation 803. That is, the electronic device may periodically acquire user heart rate information until the call is terminated, determine an emotional quotient on the basis of the acquired heart rate information, and display the determined emotional quotient.

In operation 811, when the call event is terminated, the electronic device may map the determined emotional quotient to counterpart call information. According to an embodiment, the electronic device may store an emotion quotient determined on the basis of user heart rate information acquired during an execution of a call in counterpart information for the call, such as, for example, a contact number for the contact that was just called, or the like). According to one embodiment, the electronic device may store a corresponding emotional quotient in the counterpart information in a case in which a call is performed over the reference time interval.

Figure 11:
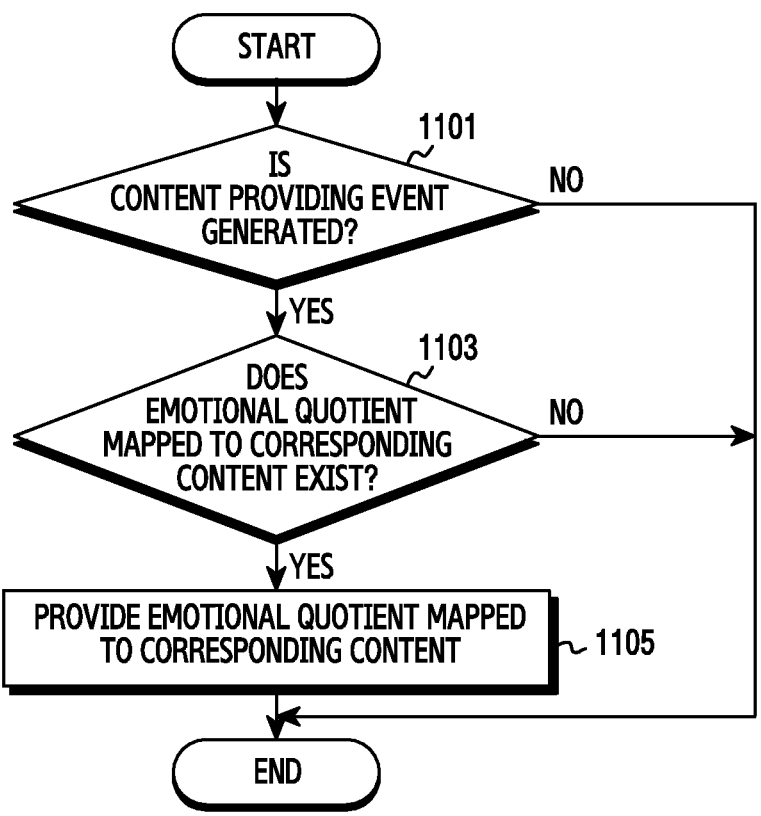
FIG. 11 is a flow chart illustrating a procedure for providing an emotional quotient mapped to a content in an electronic device according to various embodiments of the present disclosure.

FIG. 11 is a flow chart illustrating a procedure for providing an emotional quotient mapped to a content in an electronic device according to various embodiments of the present disclosure.

Referring to FIG. 11, in operation 1101, an electronic device (e.g., electronic device 101) may identify whether a content providing event is generated. According to an embodiment, a content providing event may including, for example at least one services provided by the electronic device, such as execution of a call, display of an electronic book, playback of music and/or video, and/or executing an application.

When the content providing event is generated, in operation 1103, the electronic device may identify whether an emotional quotient mapped to a corresponding content exists.

When the emotional quotient mapped to the corresponding content exists, in operation 1105, the electronic device may provide the emotional quotient mapped to the corresponding content. Hereinafter, through FIGS. 12A, 12B, 12C, 13, 14, 15, 16, 17, and 18, various embodiments for providing emotional quotient mapped to the content will be described.

FIGS. 12A, 12B, 12C, 13, 14, 15, 16, 17 and 18 are views illustrating various examples of providing an emotional quotient mapped to a content in an electronic device, according to various embodiments of the present disclosure.

Figure 12A:
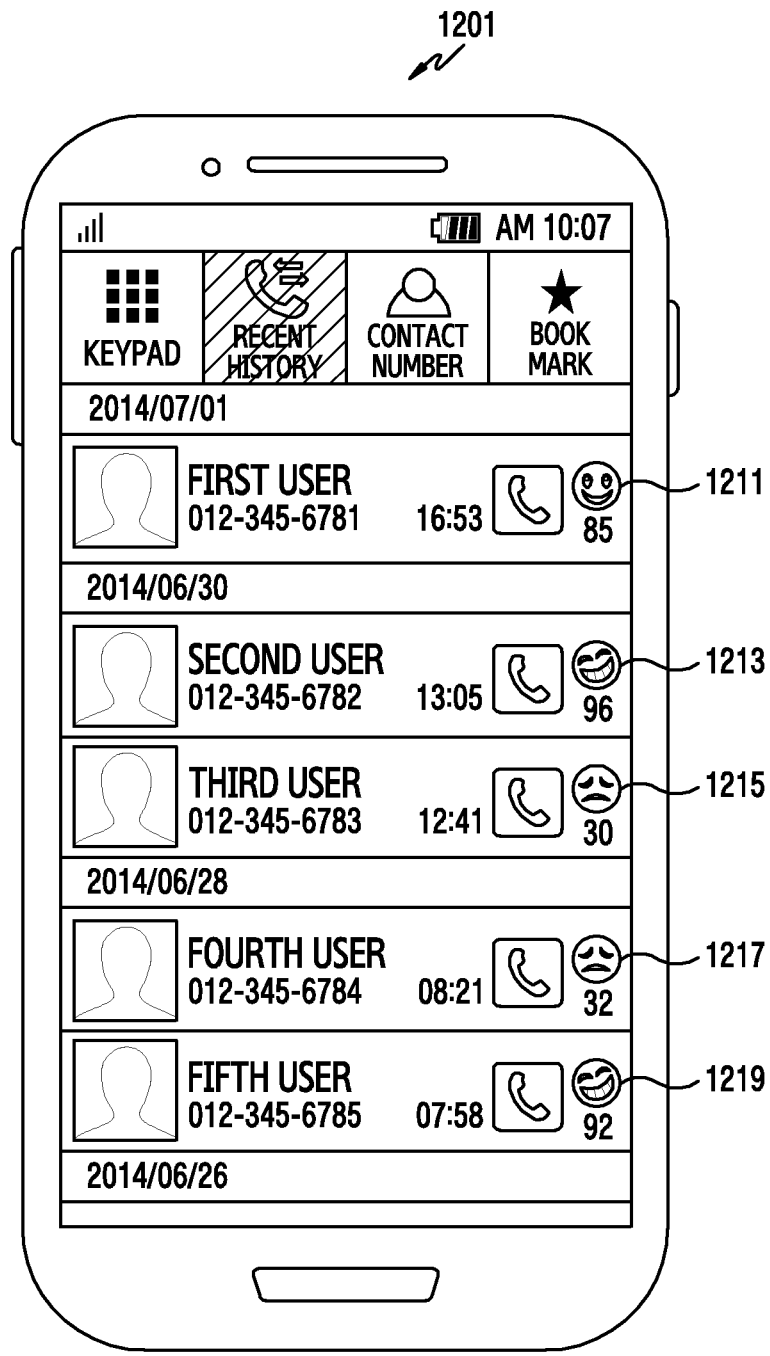
FIG. 12A, FIG. 12B, and FIG. 12C are views illustrating a method of providing an emotional quotient mapped to a content in an electronic device according to various embodiments of the present disclosure.

Referring to FIG. 12A, an electronic device 1201 may provide emotional quotients 1211, 1213, 1215, 1217, and 1219 for each respective call contact when providing a recent call history. That is, the electronic device 1201 may display an emotional quotient determined based on user heart rate information detected by the electronic device 1201 in each call with each of the "first user" to "fifth user." According to one embodiment, the electronic device 1201 may display an emotional quotient 1211-1219 determined in each call with at least one of an icon and/or a numerical value.

Figure 12B:
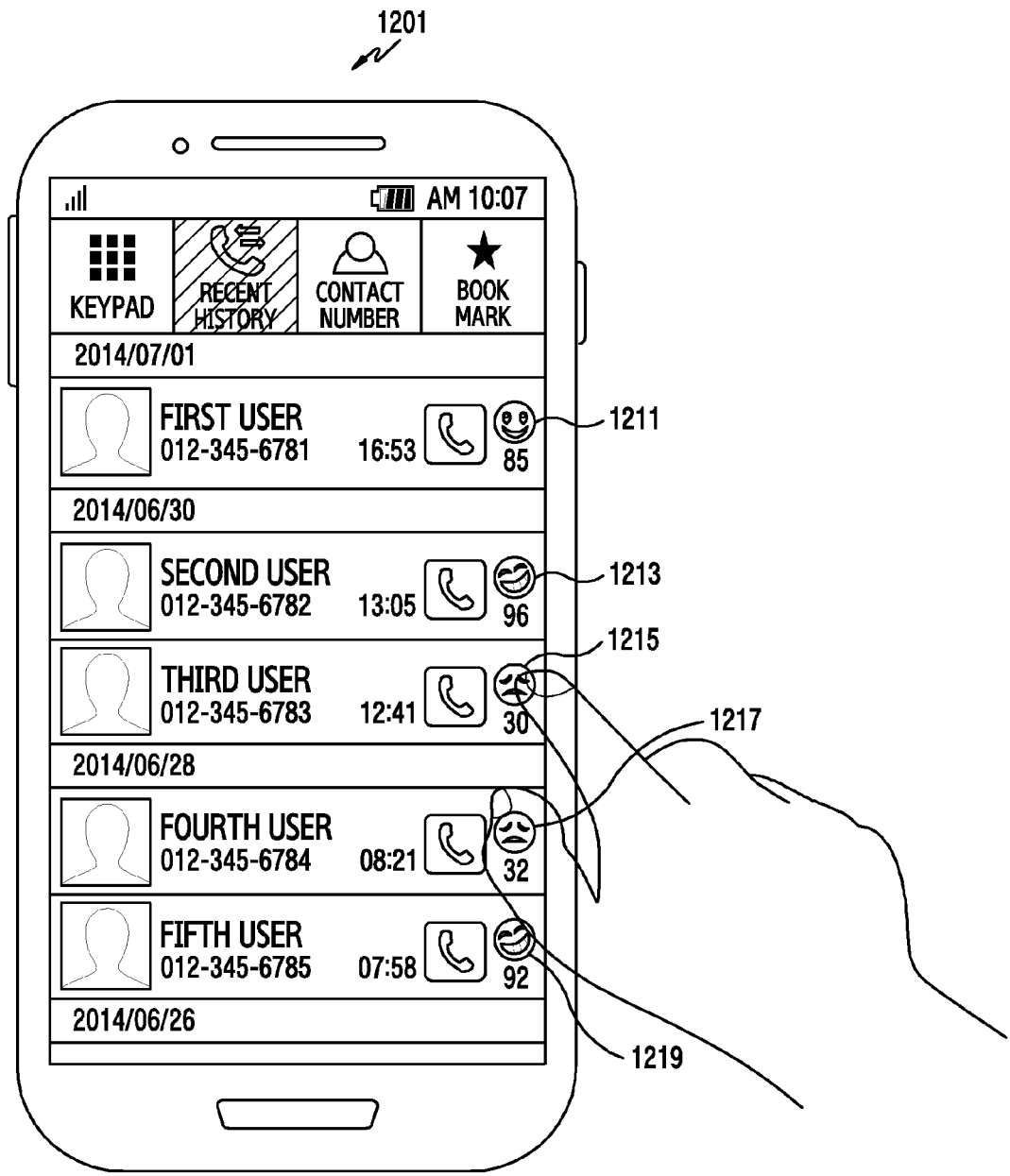
Figure 12C:
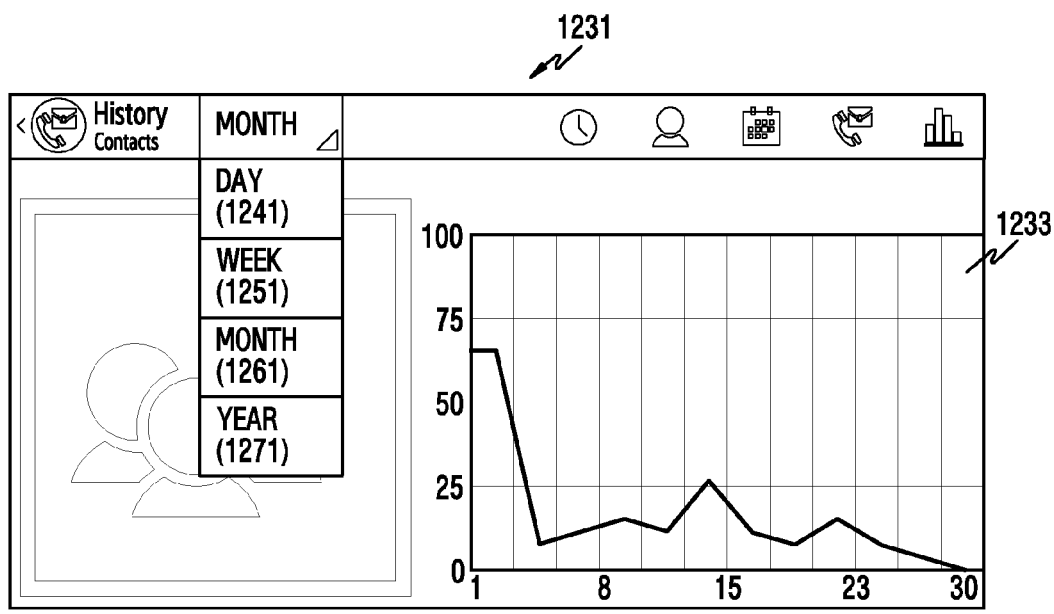

As shown in FIG. 12B and FIG. 12C, when an emotional quotient 1215 for a call with a third user in a recent call history has been selected (as seen in FIG. 12B), the electronic device may provide (or display) details 1231 (as seen in FIG. 12C) of determined in a call with the third user. According to an embodiment, an electronic device 1201 may provide (display) the details 1231 of the emotional quotient by day 1241, week 1251, month 1261, and by year 1271. According to an embodiment, the electronic device 1201 may provide the details 1231 of the emotional quotient with a graph 1233, as shown in FIG. 12C.

Figure 13:
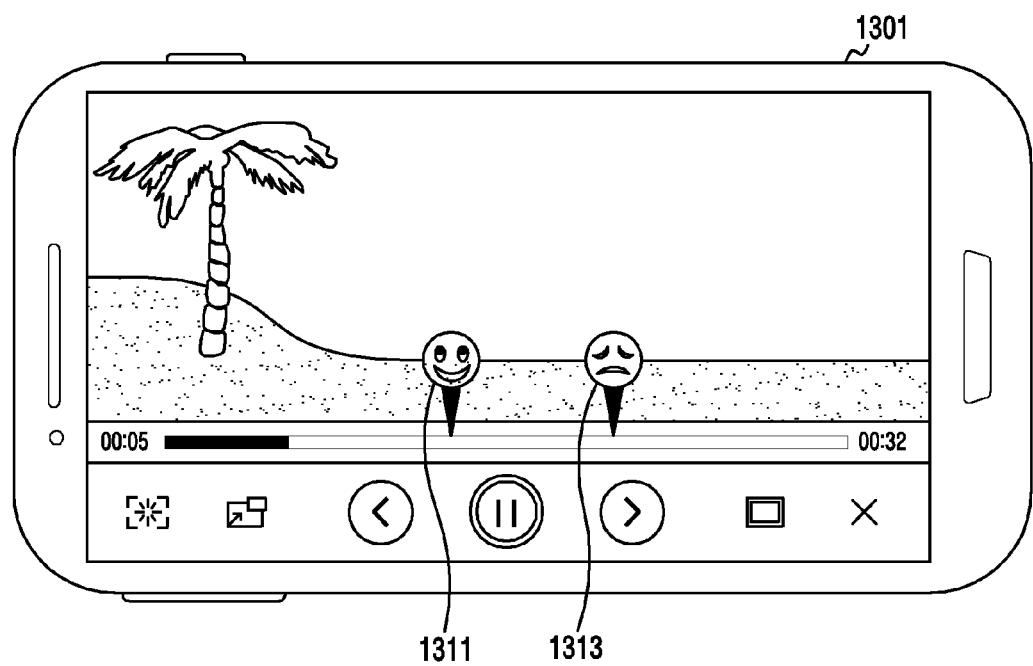
FIG. 13 is a view illustrating a method of providing an emotional quotient mapped to a content in an electronic device according to various embodiments of the present disclosure.

Referring to FIG. 13, an electronic device 1301 may provide (e.g., display) emotional quotients according to time in providing a video content. According to one embodiment, the electronic device 1301 may display icons 1311 and 1313 corresponding to and indicating emotional quotients existing at respective time points of the reproduction and playback of the video content. That is, the electronic device may map emotional quotients determined from user heart rate information to respective playback locations of a corresponding video content.

Figure 14:
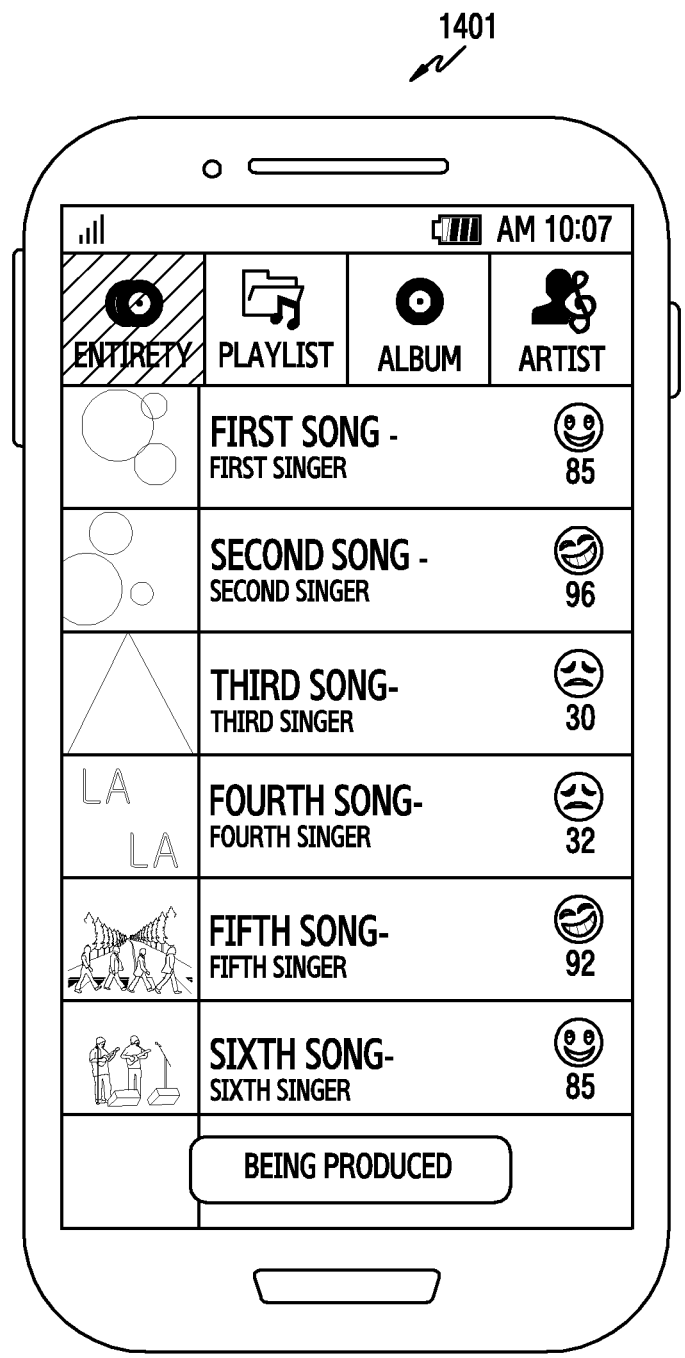
FIG. 14 is a view illustrating a method of providing an emotional quotient mapped to a content in an electronic device according to various embodiments of the present disclosure.

Referring to FIG. 14, an electronic device 1401 may provide (or display) an emotional quotient for respective songs when providing playback for audio content. That is, the electronic device may map each song to an emotional quotient determined from user heart rate information, as detected during playback of the respective corresponding song. Thus, an emotional quotient for each song may be provided when a user accesses audio content. According to one embodiment, the electronic device may arrange and display songs according to each predefined emotional quotient. According to an embodiment, the electronic device may also display a song that is similar to an emotional quotient similar to a current user emotion.

Figure 15:
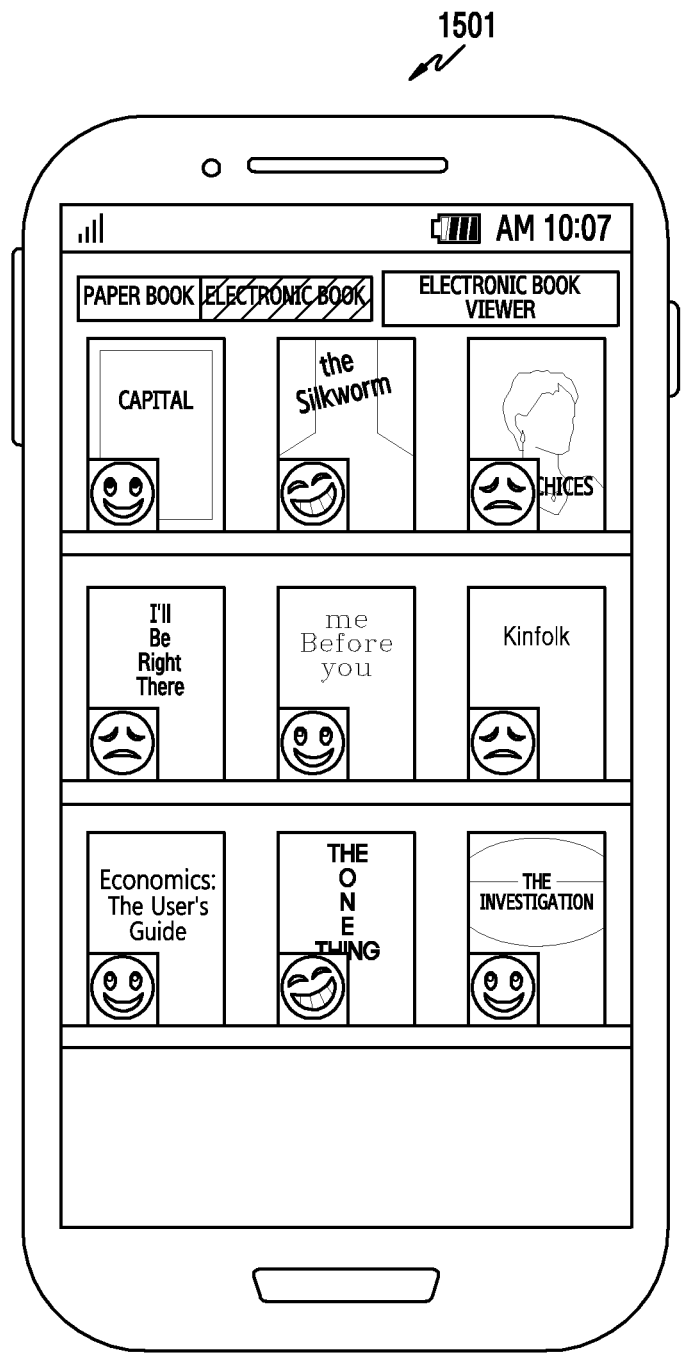
FIG. 15 is a view illustrating a method of providing an emotional quotient mapped to a content in an electronic device according to various embodiments of the present disclosure.

Referring to FIG. 15, an electronic device 1501 may provide (or display) an emotional quotient for each electronic book when providing an electronic book content. That is, the electronic device maps, to a corresponding electronic book, an emotional quotient determined from user heart rate information detected while the corresponding electronic book is provided, so that an emotional quotient for each electronic book may be provided when a user accesses the electronic book content. According to one embodiment, the electronic device may arrange and display electronic books according to each respective emotional quotient. According to one embodiment, the electronic device may display an electronic book that is mapped to an emotional quotient similar to a current user.

Figure 16:
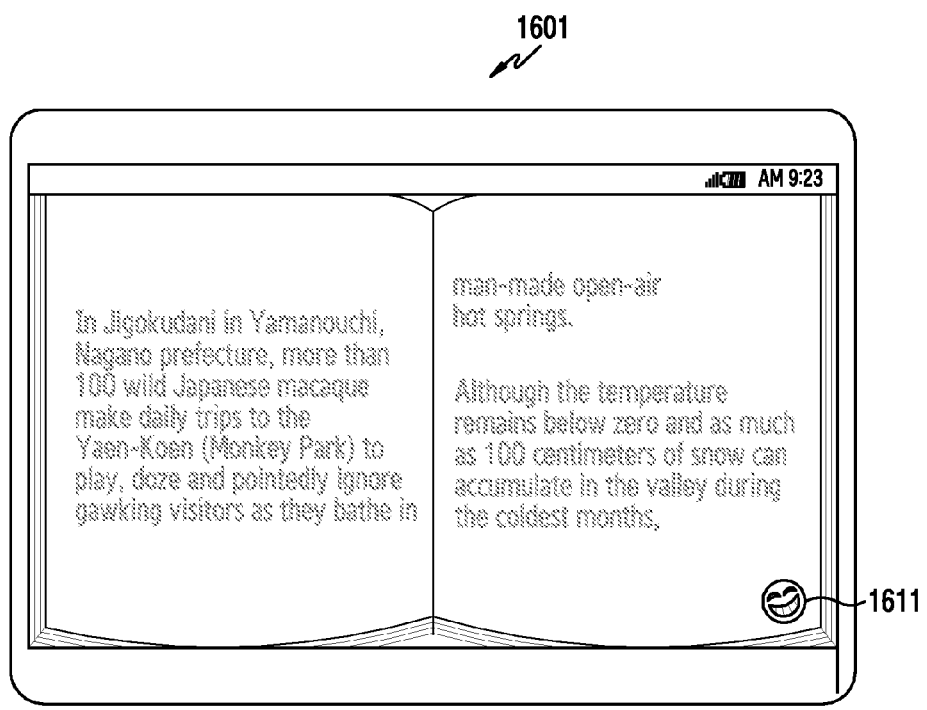
FIG. 16 is a view illustrating a method of providing an emotional quotient mapped to a content in an electronic device according to various embodiments of the present disclosure.

Referring to FIG. 16, an electronic device 1601 may provide (or display) an emotional quotient 1611 for each page during display of electronic book content. That is, the electronic device may maps to a page of a corresponding electronic book an emotional quotient determined from user heart rate information detected while the corresponding electronic book is displayed, so that an emotional quotient for each page of the electronic book may be provided when a user accesses the electronic book content. According to one embodiment, the electronic device may arrange and display pages of the electronic book according to each emotional quotient. According to one embodiment, the electronic device may display a page of the electronic book mapped to an emotional quotient similar to current user emotion.

Figure 17:
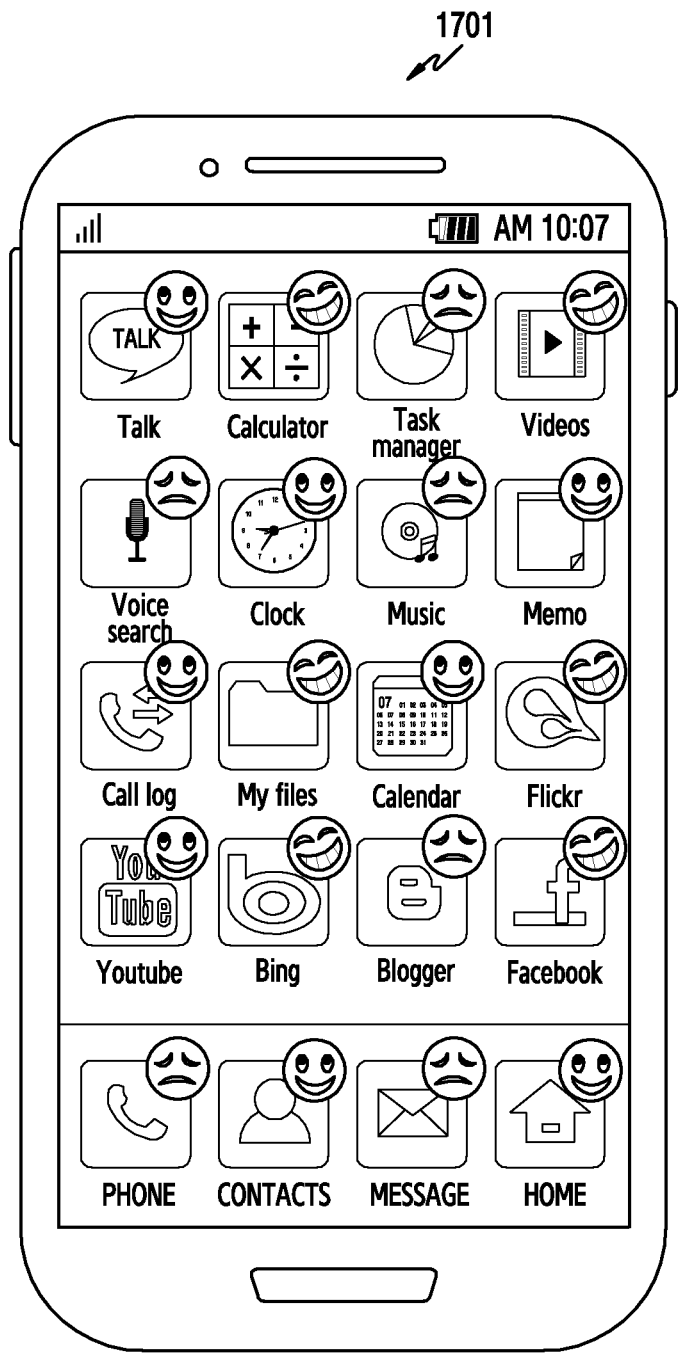
FIG. 17 is a view illustrating a method of providing an emotional quotient mapped to a content in an electronic device according to various embodiments of the present disclosure.

Referring to FIG. 17, an electronic device 1701 may provide (or display) an emotional quotient for each application in providing an application list. That is, the electronic device maps, to a corresponding application, an emotional quotient determined from user heart rate information detected while the corresponding application is executed or provided so that an emotional quotient for each application may be provided when a user accesses an application list. According to one embodiment, the electronic device may arrange and display applications according to each respective emotional quotient.

According to one embodiment, the electronic device may display an application to which an emotional quotient similar to a current user emotion is mapped.

Figure 18:
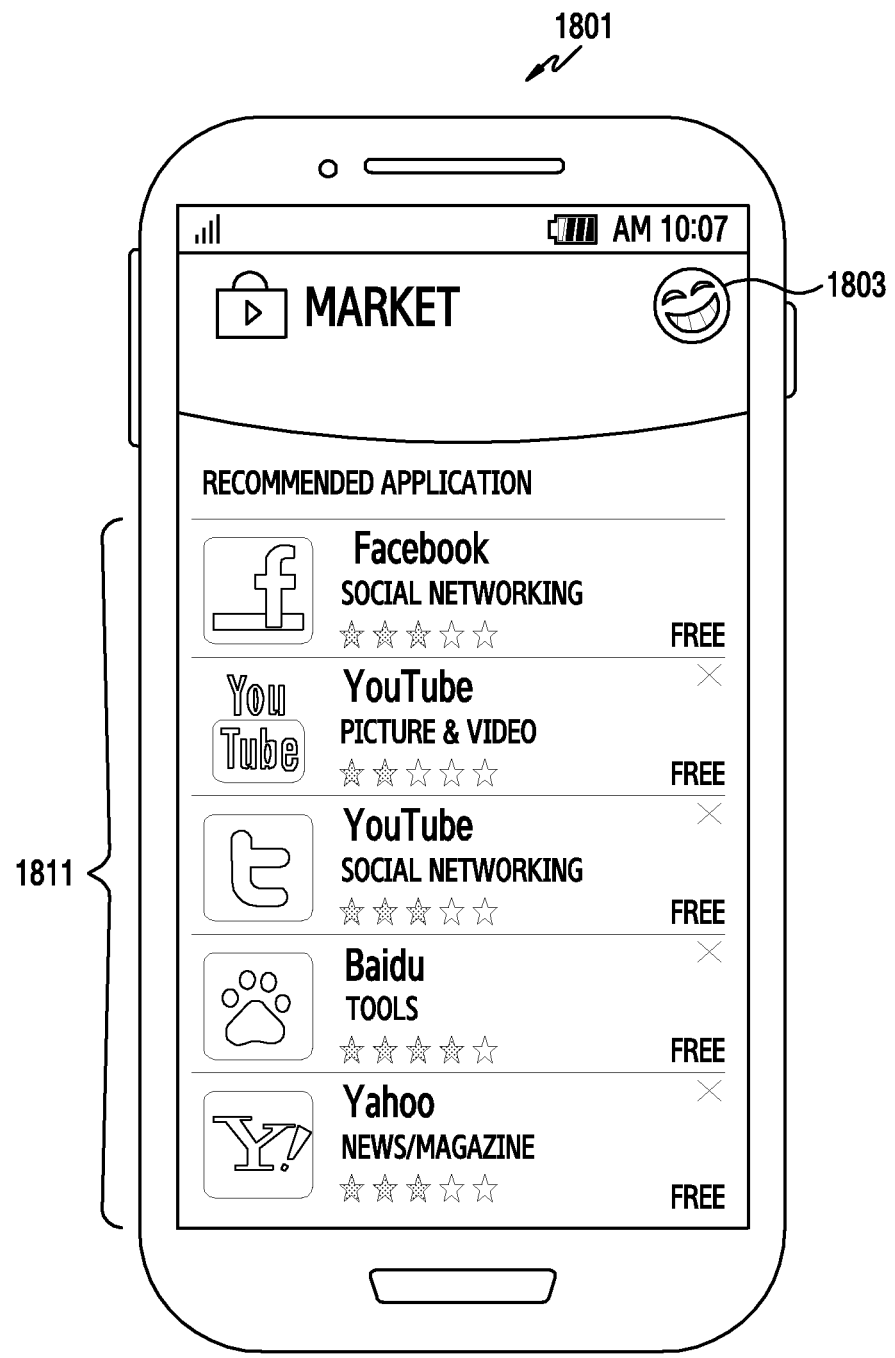
FIG. 18 is a view illustrating a method of providing an emotional quotient mapped to a content in an electronic device according to various embodiments of the present disclosure.

According to one embodiment, as shown in FIG. 18, an electronic device 1801 may identify an application mapped to an emotional quotient similar to current user emotion quotient 1803, and then recommend (or display) similar applications 1811 from, for example, an application market. According to one embodiment, the similar applications 1811 may be applications belonging to a same category in some classification of applications. According to one embodiment, the similar applications 1811 may be applications belonging to same application provider.

Figure 19:
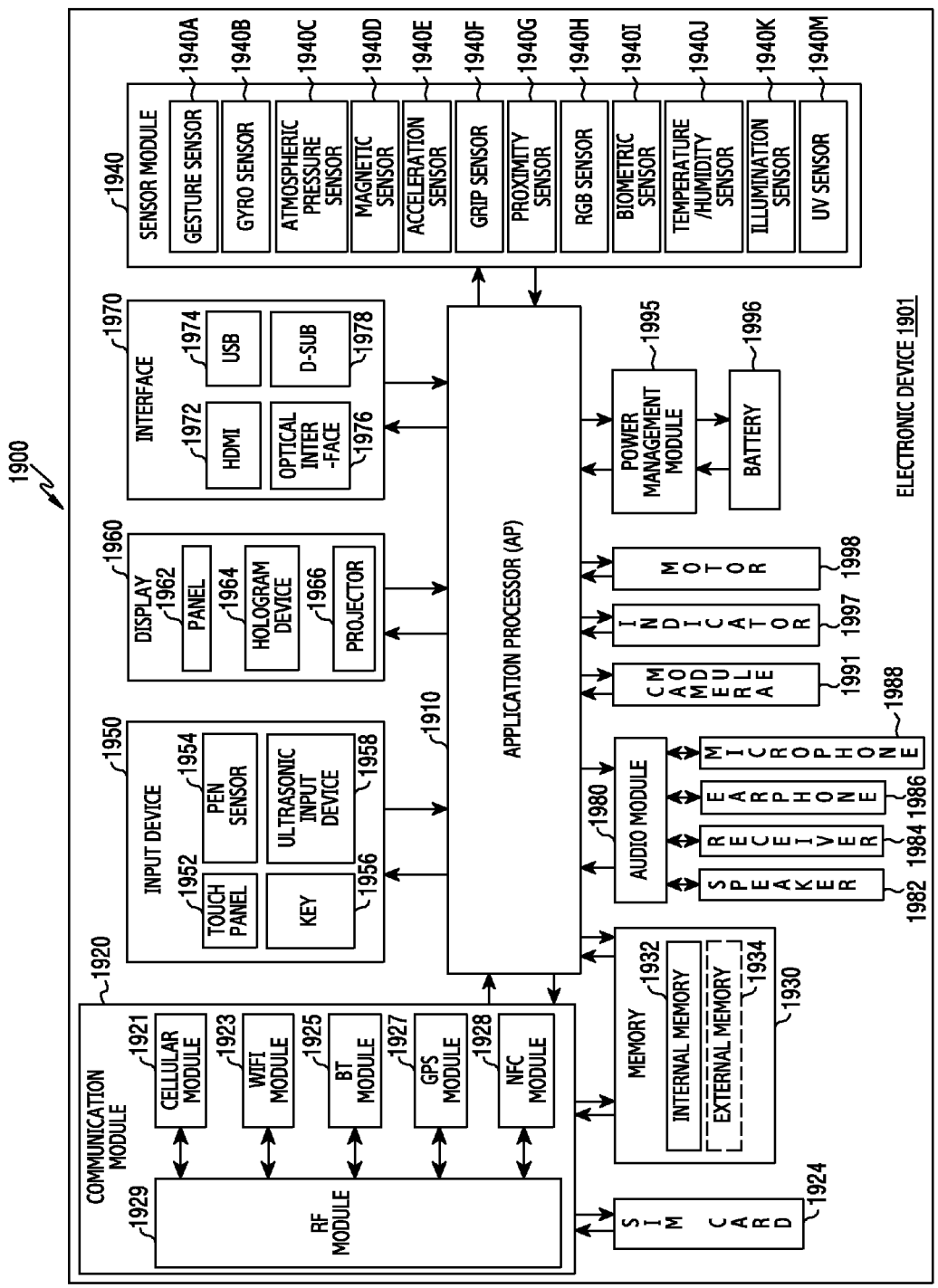
FIG. 19 is a block diagram illustrating an electronic device according to various embodiments of the present disclosure.

FIG. 19 illustrates a block diagram 1900 of an electronic device 1901 according to various embodiments of the present disclosure. The electronic device 1901 may, for example, include all or a part of the electronic device 101 shown in FIG. 1.

Referring to FIG. 19, the electronic device 1901 may include at least one Application Processor (AP) 1910, a communication module 1920, a Subscriber Identification Module (SIM) card 1924, a memory 1930, a sensor module 1940, an input device 1950, a display 1960, an interface 1970, an audio module 1980, a camera module 1991, a power management module 1995, a battery 1996, an indicator 1997, and/or a motor 1998.

The AP 1910 may control a plurality of hardware or software components connected to the AP 1910 by driving an operating system or an application program and perform processing of various pieces of data including multimedia data and calculations. The AP 1910 may, for example, be implemented by a system on chip (SoC). According to an embodiment, the AP 1910 may further include a Graphic Processing Unit (GPU).

The communication module 1920 may transmit and receive data in communication between the electronic device 1901 (for example, the electronic device 101) and other electronic devices (for example, the electronic device 104 or the server 106) connected thereto through a network. According to an embodiment, the communication module 1920 may include a cellular module 1921, a Wi-Fi module 1923, a BT module 1925, a GPS module 1927, an NFC module 1928, and a Radio Frequency (RF) module 1929.

The cellular module 1921 may provide a voice call, a video call, a text message service, or an Internet service through a communication network (for example, LTE, LTE-A, CDMA, WCDMA, UMTS, WiBro, or GSM). Further, the cellular module 1921 may perform identification and authentication of electronic devices in a communication network using, for example, a subscriber identification module (for example, the SIM card 1924). According to an embodiment, the cellular module 1921 may perform at least some functions which the AP 1910 may provide. For example, the cellular module 1921 may perform at least some of the multimedia control functions.

According to an embodiment, the cellular module 1921 may include a Communication Processor (CP). Furthermore, the cellular module 1921 may be implemented by, for example, an SoC. Although the components such as the cellular module 1921 (for example, a communication processor), the memory 1930, and the power management module 1995 are illustrated as components separate from the AP 19410 in FIG. 19, the AP 1910 may include at least some of the aforementioned components (for example, the cellular module 1921) according to one embodiment.

According to an embodiment, the AP 1910 or the cellular module 1921 (for example, the communication processor) may load a command or data received from at least one of a non-volatile memory and other components connected thereto in a volatile memory, and may process the loaded command or data. Furthermore, the AP 1910 or the cellular module 1921 may store data received from or generated by at least one of other elements in a non-volatile memory.

Each of the Wi-Fi module 1923, the BT module 1925, the GPS module 1927, and the NFC module 1928 may include, for example, a processor for processing data transmitted/received through the corresponding module. Although the cellular module 1921, the Wi-Fi module 1923, the BT module 1925, the GPS module 1927, and the NFC module 1928 are illustrated as separate blocks in FIG. 19, at least some (for example, two or more) of the cellular module 1921, the Wi-Fi module 1923, the BT module 1925, the GPS module 1927, and the NFC module 1928 may be included in one Integrated Chip (IC) or one IC package in one embodiment. For example, at least some (for example, the communication processor corresponding to the cellular module 1921 and the Wi-Fi processor corresponding to the Wi-Fi module 1923) of the processors corresponding to the cellular module 1921, the Wi-Fi module 19235, the BT module 19257, the GPS module 19278, and the NFC module 19228 may be implemented as one SoC.

The RF module 1929 may transmit/receive data, for example, an RF signal. Although not illustrated, the RF module 1929 may include, for example, a transceiver, a Power Amp Module (PAM), a frequency filter, a Low Noise Amplifier (LNA), or the like. Further, the RF module 1929 may further include a component for transmitting/receiving electronic waves over a free air space in wireless communication, for example, a conductor, a conducting wire or the like. Although the cellular module 1921, the Wi-Fi module 1923, the BT module 1925, the GPS module 1927, and the NFC module 1928 share one RF module 729 in FIG. 19, at least one of the cellular module 1921, the Wi-Fi module 1923, the BT module 1925, the GPS module 1927, and/or the NFC module 1928 may transmit/receive an RF signal through a separate RF module in one embodiment.

The SIM card 1924 may be a card including a subscriber identification module, and may be inserted into a slot formed in a particular portion of the electronic device. The SIM card 1924 may include unique identification information (for example, an Integrated Circuit Card IDentifier (ICCID)) or subscriber information (for example, an International Mobile Subscriber IDentity (IMSI)).

The memory 1930 (for example, the memory 190) may include an internal memory 1932 or an external memory 1934. The internal memory 1932 may include at least one of a volatile memory (for example, a Dynamic Random Access Memory (DRAM), a Static RAM (SRAM), a Synchronous Dynamic RAM (SDRAM), and the like) and a non-volatile memory (for example, a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, and/or the like).

According to an embodiment, the internal memory 1932 may be a Solid State Drive (SSD). The external memory 1934 may further include a flash drive, for example, a Compact Flash (CF), a Secure Digital (SD), a Micro Secure Digital (Micro-SD), a Mini Secure Digital (Mini-SD), an extreme Digital (xD), a memory stick or the like. The external memory 1934 may be functionally connected with the electronic device 1901 through various interfaces. According to an embodiment, the electronic device 1901 may further include a storage device (or a storage medium) such as a hard disc drive.

The sensor module 1940 may measure a physical quantity or detect an operation state of the electronic device 1901, and may convert the measured or detected information to an electrical signal. The sensor module 1940 may include at least one of, for example, a gesture sensor 1940A, a gyro sensor 1940B, an atmospheric pressure sensor 1940C, a magnetic sensor 1940D, an acceleration sensor 1940E, a grip sensor 1940F, a proximity sensor 1940G, a color sensor 1940H (for example, a Red/Green/Blue (RGB) sensor), a biometric sensor 1940I, a temperature/humidity sensor 1940J, an illumination sensor 1940K, and/or an Ultra Violet (UV) sensor 1940M. Additionally or alternatively, the sensor module 1940 may include, for example, an E-nose sensor (not illustrated), an electromyography (EMG) sensor (not illustrated), an electroencephalogram (EEG) sensor (not illustrated), an electrocardiogram (ECG) sensor (not illustrated), an Infrared (IR) sensor (not illustrated), an iris sensor (not illustrated), and a fingerprint sensor (not illustrated). The sensor module 1940 may further include a control circuit for controlling one or more sensors included in the sensor module.

The input device 1950 may include a touch panel 1952, a (digital) pen sensor 1954, a key 1956, or an ultrasonic input device 1958. The touch panel 1952 may recognize a touch input through at least one of, for example, a capacitive type, a resistive type, an infrared type, and/or an ultrasonic type. The touch panel 1952 may further include a control circuit. A capacitive touch panel may recognize a physical contact or proximity. The touch panel 1952 may further include a tactile layer. In this case, the touch panel 1952 may provide a tactile reaction to the user.

The (digital) pen sensor 1954 may be implemented, for example, using the same or similar method to receiving a user's touch input or using a separate recognition sheet. The key 1956 may include, for example, a physical button, an optical key, or a keypad. The ultrasonic input device 1958 may identify data by detecting an acoustic wave with a microphone (for example, a microphone 1988) of the electronic device 1901 through an input unit generating an ultrasonic signal, and may perform wireless recognition. According to an embodiment, the electronic device 1901 may receive a user input from an external device (for example, a computer or server) connected thereto using the communication module 1920.

The display 1960 may be installed to the electronic device 1901, and include a panel 1962, a hologram device 1964 or a projector 1966. The panel 1962 may be, for example, a Liquid Crystal Display (LCD), Active-Matrix Organic Light Emitting Diode (AM-OLED), or the like. The panel 1962 may be implemented to be, for example, flexible, transparent, or wearable. The panel 1962 may be configured as one module together with the touch panel 1952. The hologram device 1964 may show a stereoscopic image in the air by using interference of light. The projector 1966 may project light onto a screen to display an image. The screen may be located, for example, inside or outside the electronic device 1901. According to an embodiment, the display 1960 may further include a control circuit for controlling the panel 1962, the hologram device 1964, or the projector 1966.

The interface 1970 may include, for example, a High-Definition Multimedia Interface (HDMI) 1972, a Universal Serial Bus (USB) 1974, an optical interface 1976, or a D-subminiature (D-sub) 1978. The interface 1970 may be included in, for example, the communication interface 160 illustrated in FIG. 1. Additionally or alternatively, the interface 1970 may include, for example, a Mobile High-definition Link (MHL) interface, a Secure Digital (SD) card/Multi-Media Card (MMC) interface, or an Infrared Data Association (IrDA) standard interface.

The audio module 1980 may bilaterally convert a sound and an electrical signal. The audio module 1980 may process sound information input or output through, for example, a speaker 1982, a receiver 1984, earphones 1986, the microphone 1988 or the like.

The camera module 1991 is a device for capturing a still image or a video, and according to an embodiment, may include one or more image sensors (for example, a front sensor or a rear sensor), a lens (not illustrated), an Image Signal Processor (ISP) (not illustrated), or a flash (not illustrated) (for example, an LED or xenon lamp).

The power management module 1995 may manage power of the electronic device 1901. Although not illustrated, the power management module 1995 may include, for example, a Power Management Integrated Circuit (PMIC), a charger Integrated Circuit (IC), or a battery or fuel gauge. The PMIC may be mounted to, for example, an integrated circuit or an SoC semiconductor.

Charging methods may be classified into a wired charging method and a wireless charging method. The charger IC may charge a battery and prevent over voltage or over current from a charger. According to an embodiment, the charger IC may include a charger IC for at least one of the wired charging method and/or the wireless charging method. Examples of the wireless charging may include magnetic resonance charging, magnetic induction charging, and electromagnetic charging, and an additional circuit such as a coil loop, a resonance circuit, and a rectifier may be added for the wireless charging.

The battery gauge may measure, for example, a remaining quantity of the battery 1996, or a voltage, a current, or a temperature during the charging. The battery 1996 may store or generate electricity, and may supply power to the electronic device 1901 using the stored or generated electricity. The battery 1996 may include, for example, a rechargeable battery or a solar battery.

The indicator 1997 may display a specific status of the electronic device 1901 or the part (for example, the AP 1910) of electronic device 1901, for example, a booting status, a message status, a charging status, and the like. The motor 1998 may convert an electrical signal to a mechanical vibration. Although not illustrated, the electronic device 1901 may include a processing unit (for example, a GPU) for supporting mobile TV. The processing unit for supporting mobile TV may process media data according to a standard of Digital Multimedia Broadcasting (DMB), Digital Video Broadcasting (DVB), media flow or the like.

According to various embodiments, an electronic device maps an emotional quotient determined on the basis of measured heart rate information to a content when a content is provided so that an emotional quotient mapped to a corresponding content may easily be identified when a user uses the corresponding content.

The above described components of the electronic device according to various embodiments of the present disclosure may be formed of one or more components, and a name of a corresponding component element may be changed based on the type of electronic device. The electronic device according to the present disclosure may include one or more of the aforementioned components or may further include other additional components, or some of the aforementioned components may be omitted. Further, some of the components of the electronic device according to the various embodiments of the present disclosure may be combined to form a single entity, and thus, may equivalently execute functions of the corresponding elements prior to the combination.

The "module" used in various embodiments of the present disclosure may refer to, for example, a "unit" including one of hardware, software, and firmware, or a combination of two or more of the hardware, software, and firmware. The "module" may be interchangeably used with a term, such as unit, logic, logical block, component, or circuit. The "module" may be the smallest unit of an integrated component or a part thereof. The "module" may be the smallest unit that performs one or more functions or a part thereof The "module" may be mechanically or electronically implemented. For example, the "module" according to various embodiments of the present disclosure may include at least one of an Application-Specific Integrated Circuit (ASIC) chip, a Field-Programmable Gate Arrays (FPGAs), and a programmable-logic device for performing operations which have been known or are to be developed hereafter.

According to various embodiments, at least some of the devices (for example, modules or functions thereof) or the method (for example, operations) according to the present disclosure may be implemented by a command stored in a computer-readable storage medium in a programming module form. When he command is executed by one or more processors (for example, the processor 120), the one or more processors may execute a function corresponding to the command. The computer-readable storage medium may be, for example, the memory 190. At least a part of the programming module may, for example, be implemented (e.g., executed) by the processor 120. At least some of the programming modules may include, for example, a module, a program, a routine, a set of instructions or a process for performing one or more functions.

The computer readable recoding medium may include magnetic media, such as a hard disk, a floppy disk and a magnetic tape, optical media, such as a Compact Disc Read Only Memory (CD-ROM) and a Digital Versatile Disc (DVD), magneto-optical media, such as a floptical disk, and a hardware device specially configured to store and execute a program instruction (for example, a programming module), such as a Read Only Memory (ROM), a Random Access Memory (RAM), a flash memory, and the like. In addition, the program instructions may include high class language codes, which can be executed in a computer by using an interpreter, as well as machine codes made by a compiler. The aforementioned hardware device may be configured to operate as one or more software modules in order to perform the operation of various embodiments of the present disclosure, and vice versa.

A module or a programming module according to the present disclosure may include at least one of the described component elements, a few of the component elements may be omitted, or additional component elements may be included. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

The embodiments of the present disclosure disclosed in the specification and the drawings are only particular examples proposed in order to easily describe the technical matters of the present disclosure and help with comprehension of the present disclosure, and do not limit the present disclosure. Therefore, in addition to the embodiments disclosed herein, the various embodiments of the present disclosure should be construed to include all modifications or modified forms drawn based on the technical idea of the various embodiments of the present disclosure.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for". In addition, an artisan understands and appreciates that a "processor" or "microprocessor" may be hardware in the claimed disclosure. Under the broadest reasonable interpretation, the appended claims are statutory subject matter in compliance with 35 U.S.C. §101.

What is claimed is:

1. A method in an electronic device, comprising:
receiving, by a communication module of the electronic device, a heart rate information of a user of the electronic device from an external electronic device operatively coupled to the electronic device during a duration when the user of the electronic device performs a call with a user of another electronic device, wherein the heart rate information of the user is detected using a first sensor of the external electronic device;
determining, by a processor of the electronic device, an emotional quotient of the user by calculating an average of numerical values representing emotional quotients corresponding to the heart rate information detected during the duration; and mapping the determined emotional quotient to a provided content.

2. The method of claim 1, wherein a second sensor is included in the electronic device.

3. The method of claim 2, wherein the first sensor and the second sensor are heart rate measurement sensors, and further comprising:

activating the second sensor; and detecting the heart rate information of the user using the activated second sensor.

4. The method of claim 1, further comprising:

displaying on a display of the electronic device the determined emotional quotient that is mapped to the content while the content is provided.

5. The method of claim 4, wherein the determined emotional quotient that is mapped to the content is displayed using at least one of an icon and a numerical value representing the determined emotional quotient.

6. The method of claim 4, wherein the emotion quotient mapped to the content is displayed while the content is provided on the display which is included in the electronic device.

7. The method of claim 4, wherein the emotion quotient mapped to the content is displayed while the content is provided through the display which is included in an external electronic device operatively coupled to the electronic device.

8. The method of claim 1, further comprising:

identifying whether a stored emotional quotient that is mapped to the provided content exists; and when the stored emotional quotient that is mapped to the content exists, displaying on the display the stored emotional quotient that is mapped to the content.

9. The method of claim 8, wherein the stored emotion quotient mapped to the content is displayed on the display which is included in the electronic device.

10. The method of claim 8, wherein the stored emotion quotient mapped to the content is displayed through the display which is included in an external electronic device operatively coupled to the electronic device.

11. An electronic device comprising:

a communication module;

a display; and a processor configured to:

receive, by the communication module of the electronic device, a heart rate information of a user of the electronic device from an external electronic device operatively coupled to the electronic device during a duration when the user of the electronic device performs a call with a user of another electronic device, wherein the heart rate information of the user is detected using a first sensor of the external electronic device;

determine an emotional quotient by calculating an average of numerical values representing emotional quotients corresponding to the heart rate information detected during the duration; and map the determined emotional quotient to a provided content.

12. The electronic device of claim 11, wherein the processor is further configured to detect the heart rate information through a second sensor which is included in the electronic device.

13. The electronic device of claim 12, wherein the first sensor and the second sensor are a heart rate measurement sensors, the processor further configured to:

detect the heart rate information by activating the second sensor of the electronic device.

14. The electronic device of claim 11, wherein the processor is further configured to control the display to display the determined emotion quotient that is mapped to the content while the content is provided.

15. The electronic device of claim 14, wherein the processor is further configured to control the display to display the determined emotion quotient using at least one of an icon and a numerical value.

16. The electronic device of claim 14, wherein the processor is further configured to control the display to display the emotion quotient mapped to the content while the content is provided.

17. The electronic device of claim 14, wherein the processor is further configured to control a second display installed to an external electronic device operatively coupled to the electronic device to display the determined emotion quotient that is mapped to the content while the content is provided.

18. The electronic device of claim 11, wherein the processor is further configured to provide the content by:

identifying whether a stored emotion quotient that is mapped to the provided content exists; and when the stored emotion quotient that is mapped to the content exists, controlling the display to display the stored emotion quotient that is mapped to the content.

19. The electronic device of claim 18, wherein the processor is further configured to control the display to display the stored emotion quotient mapped to the content.

20. The electronic device of claim 18, wherein the processor is further configured to display the stored emotion quotient mapped to the content through a second display which is included in an external electronic device operatively coupled to the electronic device.

* * * * *